(12) United States Patent
Zaltsman et al.

(10) Patent No.: US 12,317,892 B2
(45) Date of Patent: *Jun. 3, 2025

(54) MICRO AND NANOPARTICULATE COMPOSITIONS COMPRISING ANTI-MICROBIALLY ACTIVE GROUPS

(71) Applicants: NOBIO LTD., Kadima (IL); HADASIT MEDICAL RESEARCH SERVICES AND DEVELOPMENT LTD., Jerusalem (IL)

(72) Inventors: Nathan Zaltsman, Hadera (IL); Ervin Itzhak Weiss, Herzliya (IL); Nurit Beyth, Jerusalem (IL)

(73) Assignees: Nobio Ltd., Kadima (IL); Hadasit Medical Research Services And Development Ltd., Jerusalem (IL)

( * ) Notice: Subject to any disclaimer, the term of this patent is extended or adjusted under 35 U.S.C. 154(b) by 294 days.

This patent is subject to a terminal disclaimer.

(21) Appl. No.: 17/531,957

(22) Filed: Nov. 22, 2021

(65) Prior Publication Data

US 2022/0225612 A1    Jul. 21, 2022

Related U.S. Application Data

(63) Continuation of application No. 16/079,283, filed as application No. PCT/IL2017/050240 on Feb. 26, 2017, now Pat. No. 11,178,867.

(51) Int. Cl.
A61K 47/69 (2017.01)
A01N 25/12 (2006.01)
(Continued)

(52) U.S. Cl.
CPC ............. *A01N 33/12* (2013.01); *A01N 25/12* (2013.01); *A61K 6/80* (2020.01); *A61K 8/25* (2013.01);
(Continued)

(58) Field of Classification Search
CPC .................................. A01N 33/12; A61K 8/25
See application file for complete search history.

(56) References Cited

U.S. PATENT DOCUMENTS 3,972,855 A   8/1976 Martinsson et al.
4,144,122 A   3/1979 Emanuelsson et al.
(Continued)

FOREIGN PATENT DOCUMENTS

CA       2799833 C      4/2016
CN       101355922      1/2009
(Continued)

OTHER PUBLICATIONS

Abramovitz, I., et al. (2013). Antibacterial temporary restorative materials incorporating polyethyleneimine nanoparticles. Quintessence international, 44(3).

(Continued)

*Primary Examiner* — Isaac Shomer
(74) *Attorney, Agent, or Firm* — PEARL COHEN ZEDEK LATZER BARATZ LLP

(57) ABSTRACT

The present invention relates to anti-microbially active micro and nanoparticles, compositions comprising same, and use thereof for inhibiting bacterial growth and biofilm formation on surfaces or devices, e.g., dental surfaces or devices. The present invention further discloses methods of making such anti-microbially active micro or nanoparticles.

18 Claims, 11 Drawing Sheets

(51) Int. Cl.
  *A01N 33/12* (2006.01)
  *A61K 6/80* (2020.01)
  *A61K 8/25* (2006.01)
  *A61K 8/41* (2006.01)
  *C08K 9/04* (2006.01)
(52) U.S. Cl.
  CPC .......... *A61K 8/416* (2013.01); *A61K 47/6923* (2017.08); *A61K 47/6929* (2017.08); *C08K 9/04* (2013.01)

(56) References Cited

U.S. PATENT DOCUMENTS

| | | |
|---|---|---|
| 5,277,136 A | 1/1994 | Davis |
| 5,408,022 A | 4/1995 | Imazato et al. |
| 5,494,987 A | 2/1996 | Imazato et al. |
| 5,672,368 A | 9/1997 | Perkins |
| 5,672,638 A | 9/1997 | Verhoeven et al. |
| 5,733,949 A | 3/1998 | Imazato et al. |
| 5,798,117 A | 8/1998 | New et al. |
| 5,954,869 A | 9/1999 | Elfersy et al. |
| 5,980,868 A | 11/1999 | Homola et al. |
| 6,039,940 A | 3/2000 | Perrault et al. |
| 6,113,815 A | 9/2000 | Elfersy et al. |
| 6,120,587 A | 9/2000 | Elfersy et al. |
| 6,123,925 A | 9/2000 | Barry et al. |
| 6,146,688 A | 11/2000 | Morgan et al. |
| 6,183,248 B1 | 2/2001 | Chishti et al. |
| 6,251,967 B1 | 6/2001 | Perichaud et al. |
| 6,355,704 B1 | 3/2002 | Nakatsuka et al. |
| 6,482,402 B1 | 11/2002 | Kurtz et al. |
| 6,559,116 B1 | 5/2003 | Godfroid et al. |
| 6,562,330 B1 | 5/2003 | Stratford et al. |
| 6,572,926 B1 | 6/2003 | Morgan et al. |
| 6,607,382 B1 | 8/2003 | Kuo et al. |
| 6,762,172 B1 | 7/2004 | Elfersy et al. |
| 6,929,818 B2 | 8/2005 | Luthra et al. |
| 7,115,421 B2 | 10/2006 | Grzeda et al. |
| 7,709,694 B2 | 5/2010 | Batich et al. |
| 7,771,743 B1 | 8/2010 | Luthra et al. |
| 7,799,888 B2 | 9/2010 | Arkles et al. |
| 7,851,653 B2 | 12/2010 | Getman et al. |
| 7,858,141 B2 | 12/2010 | Getman et al. |
| 8,389,021 B2 | 3/2013 | Baker |
| 8,439,674 B2 | 5/2013 | Li et al. |
| 8,455,599 B2 | 6/2013 | Arkles et al. |
| 8,535,645 B2 | 9/2013 | Domb et al. |
| 8,999,291 B2 | 4/2015 | Goodman et al. |
| 9,011,979 B2 | 4/2015 | Pansera et al. |
| 9,314,407 B2 | 4/2016 | Blizzard et al. |
| 9,624,384 B2 | 4/2017 | Mason et al. |
| 9,744,120 B2 | 8/2017 | Neigel |
| 10,010,080 B2 | 7/2018 | Neigel |
| 10,159,630 B2 | 12/2018 | Blizzard et al. |
| 10,328,020 B1 | 6/2019 | Neigel |
| 10,405,553 B1 | 9/2019 | Mason et al. |
| 10,531,664 B2 | 1/2020 | Mason et al. |
| 11,134,676 B2 * | 10/2021 | Zaltsman .................. C08K 9/04 |
| 11,178,867 B2 * | 11/2021 | Zaltsman .................. C08K 9/04 |
| 11,384,172 B2 | 7/2022 | Naruse et al. |
| 2004/0077892 A1 | 4/2004 | Arkles et al. |
| 2004/0161390 A1 * | 8/2004 | Gallis .................... A61Q 11/00 |
| | | 424/49 |
| 2004/0180093 A1 | 9/2004 | Burton et al. |
| 2005/0079150 A1 | 4/2005 | Gellman et al. |
| 2005/0277752 A1 | 12/2005 | Bringley |
| 2006/0018966 A1 | 1/2006 | Lin et al. |
| 2006/0115782 A1 | 6/2006 | Li et al. |
| 2006/0115785 A1 | 6/2006 | Li et al. |
| 2007/0258996 A1 | 11/2007 | Pradip et al. |
| 2007/0299538 A1 | 12/2007 | Roeber |
| 2008/0069887 A1 | 3/2008 | Baran et al. |
| 2008/0226728 A1 * | 9/2008 | Domb ...................... A61K 6/69 |
| | | 977/906 |
| 2009/0285886 A1 | 11/2009 | Van Beek |
| 2010/0004202 A1 | 1/2010 | Chisholm et al. |
| 2013/0230676 A1 * | 9/2013 | Blizzard ................ C08G 77/58 |
| | | 521/154 |
| 2014/0308330 A1 | 10/2014 | Santra et al. |
| 2014/0322287 A1 | 10/2014 | Onis et al. |
| 2016/0051450 A1 | 2/2016 | Kashiki et al. |
| 2016/0135470 A1 | 5/2016 | Agrawal et al. |
| 2016/0235631 A1 | 8/2016 | Nojiri |
| 2018/0362714 A1 | 12/2018 | Grubbs et al. |
| 2019/0053487 A1 | 2/2019 | Zaltsman et al. |
| 2020/0236931 A1 | 7/2020 | Trainor et al. |

FOREIGN PATENT DOCUMENTS

| | | |
|---|---|---|
| CN | 102469776 | 5/2012 |
| CN | 103374093 | 10/2013 |
| CN | 102838085 B | 4/2014 |
| CN | 102549082 B | 1/2015 |
| CN | 105940062 | 9/2016 |
| CN | 106567259 A | 4/2017 |
| DE | 102012003117 A1 | 8/2013 |
| DE | 102009047589 | 1/2014 |
| EP | 0360962 A2 | 4/1990 |
| EP | 0537774 | 4/1993 |
| EP | 0688901 A2 | 12/1995 |
| EP | 0705590 A1 | 4/1996 |
| EP | 0607195 B1 | 4/1999 |
| EP | 0908189 A2 | 4/1999 |
| EP | 1042005 A2 | 10/2000 |
| EP | 0980682 B1 | 11/2003 |
| EP | 1863865 B1 | 5/2012 |
| EP | 2450058 A1 | 5/2012 |
| EP | 1841314 B1 | 3/2014 |
| EP | 3269771 A1 | 1/2018 |
| EP | 3675802 | 7/2020 |
| FR | 3071729 A1 | 4/2019 |
| JP | 53130428 | 11/1978 |
| JP | 02307913 | 12/1990 |
| JP | 05209020 | 8/1993 |
| JP | 05229975 | 9/1993 |
| JP | 06341013 | 12/1994 |
| JP | 07206621 | 8/1995 |
| JP | 07215814 | 8/1995 |
| JP | 08253637 | 10/1996 |
| JP | 10025218 | 1/1998 |
| JP | 10139797 | 5/1998 |
| JP | 10204727 | 8/1998 |
| JP | 10236914 | 9/1998 |
| JP | 10236915 | 9/1998 |
| JP | 2000063290 | 2/2000 |
| JP | 2001009464 A | 1/2001 |
| JP | 2002122827 | 4/2002 |
| JP | 2003104435 | 4/2003 |
| JP | 2003286151 | 10/2003 |
| JP | 2003301055 | 10/2003 |
| JP | 2005179238 | 7/2005 |
| JP | 2007269637 | 10/2007 |
| JP | 2008184431 | 8/2008 |
| JP | 2011038195 | 2/2011 |
| JP | 4783707 B2 | 9/2011 |
| JP | 2013/501742 | 1/2013 |
| JP | 2014001166 A | 1/2014 |
| JP | 2018002642 A | 1/2018 |
| KR | 10-2012-0117760 | 10/2012 |
| KR | 10-2013-0124165 | 11/2013 |
| KR | 10-2015-0115757 | 10/2015 |
| KR | 20180006705 A | 1/2018 |
| WO | WO 1993/020775 A1 | 10/1993 |
| WO | WO 1995/010940 A1 | 4/1995 |
| WO | WO 2001/090251 | 11/2001 |
| WO | WO-2005/023931 | 3/2005 |
| WO | WO 2005/123612 A2 | 12/2005 |
| WO | WO-2006/070376 | 7/2006 |
| WO | WO 2008/049250 A1 | 5/2008 |
| WO | WO 2008/149505 | 12/2008 |
| WO | WO 2009/027971 A2 | 3/2009 |
| WO | WO 2009/091001 | 7/2009 |
| WO | WO 2010/091124 A2 | 8/2010 |
| WO | WO 2011/036031 A1 | 3/2011 |

(56) References Cited

FOREIGN PATENT DOCUMENTS

| | | |
|---|---|---|
| WO | WO 2011/020586 | 8/2011 |
| WO | WO 2011/097347 A2 | 8/2011 |
| WO | WO 2011/150001 | 12/2011 |
| WO | WO 2012/021754 A2 | 2/2012 |
| WO | WO 2014/058757 A2 | 8/2014 |
| WO | WO-2014/121189 | 8/2014 |
| WO | WO 2015/104894 | 7/2015 |
| WO | WO-2016/073634 | 5/2016 |
| WO | WO 2016/172436 A1 | 10/2016 |
| WO | WO 2017/078622 A1 | 5/2017 |
| WO | WO 2017/145142 A1 | 8/2017 |
| WO | WO 2017/145167 A1 | 8/2017 |
| WO | WO-2017/104676 | 7/2018 |
| WO | WO-2019/043713 | 3/2019 |
| WO | WO 2019/078198 A1 | 4/2019 |

OTHER PUBLICATIONS

Beyth, N., et al. (2006). Antibacterial activity of dental composites containing quaternary ammonium polyethylenimine nanoparticles against *Streptococcus* mutans. Biomaterials, 27(21), 3995-4002.
Beyth, N., et al. (2010). Long-term antibacterial surface properties of composite resin incorporating polyethyleneimine nanoparticles. Quintessence international, 41(10).
Beyth, N., et al. (2010). Polyethyleneimine nanoparticles incorporated into resin composite cause cell death and trigger biofilm stress in vivo. Proceedings of the National Academy of Sciences, 107(51), 22038-22043.
Beyth, N., et al. (2012). Antibacterial activity of dental cements containing quaternary ammonium polyethyleneimine nanoparticles. Journal of Nanomaterials, 2012, 58.
Beyth, N., et al. (2013). Rapid Kill—Novel Endodontic Sealer and Enterococcus faecalis. PloS one, 8(11), e78586.
Beyth, N., et al. (2014). Antibacterial dental resin composites. Reactive and Functional Polymers, 75, 81-88.
Beyth, N., et al. (2018). Antimicrobial nanoparticles in restorative composites. In Emerging Nanotechnologies in Dentistry (pp. 35-47). William Andrew Publishing.
Beyth, S., et al. (2013). Antibacterial activity of bone cement containing quaternary ammonium polyethyleneimine nanoparticles. Journal of Antimicrobial Chemotherapy, 69(3), 854-855.
Biosafe. Technical Guide for Performance and Regulatory Compliance—Organosilane Antimicrobials; Provides long-lasting surface protection. Downloaded on Feb. 2017.
Busscher, H. J., et al. (2010). Biofilm formation on dental restorative and implant materials. Journal of dental research, 89(7), 657-665.
Carpenter, A. W., et al. (2012). Dual action antimicrobials: nitric oxide release from quaternary ammonium-functionalized silica nanoparticles. Biomacromolecules, 13(10), 3334-3342.
Domb, A. J., et al. (2013). Quaternary Ammonium Antimicrobial Polymers. MRS Online Proceedings Library Archive, 1569, 97-107.
Farah, S., et al. (2013). Crosslinked QA-PEI nanoparticles: synthesis reproducibility, chemical modifications, and stability study. Polymers for Advanced Technologies, 24(5), 446-452.
Farah, S., et al. (2014). Antimicrobial silica particles loaded with quaternary ammonium polyethyleneimine network. Polymers for Advanced Technologies, 25(6), 689-692.
Imazato et al., (2000). Cytotoxic effects of composite restorations employing self-etching primers or experimental antibacterial primers. Journal of dentistry, 28(1), 61-67. (Only abstract).
Imazato et al., (2002). Penetration of an antibacterial dentine-bonding system into demineralized human root dentine in vitro. European journal of oral sciences, 110(2), 168-174. (Only abstract).
Imazato et al., (2003). Antibacterial activity of bactericide-immobilized filler for resin-based restoratives. Biomaterials, 24(20), 3605-3609.
International Search Report issued for PCT Application No. PCT/IL2006/000005 dated Mar. 13, 2006.
International Search Report issued for PCT Application No. PCT/IL2016/050219 dated Jun. 16, 2016.
International Search Report issued for PCT Application No. PCT/IL2017/050240 dated Jun. 19, 2017.
International Search Report issued for PCT Application No. PCT/IL2018/050969 dated Nov. 12, 2018.
International Search Report issued for PCT Application No. PCT/IL2018/050970 dated Nov. 11, 2018.
Ionescu, A., et al. (2012). Influence of surface properties of resin-based composites on in vitro *Streptococcus mutans* biofilm development. European journal of oral sciences, 120(5), 458-465. (Only abstract).
Jung et al. "Quantitative Analysis and Efficient Surface Modification of Silica Nanoparticles." Journal of Nanomaterials, vol. 2012, Article ID 593471, pp. 1-8; and Supplementary Information, pp. 1-5. (Year: 2012).
Kataev et al. (2014). Quaternary ammonium derivatives of natural terpenoids. Synthesis and properties. Russian Chemical Bulletin, 63(9), 1884-1900.
Kawabata, N., et al. (1988). Antibacterial activity of soluble pyridinium-type polymers. Appl. Environ. Microbiol., 54(10), 2532-2535.
Kenawy, E. R., et al. (2006). Biologically active polymers: VII. Synthesis and antimicrobial activity of some crosslinked copolymers with quaternary ammonium and phosphonium groups. Reactive and Functional Polymers, 66(4), 419-429.
Kim, H. W., et al. (2010). Imparting durable antimicrobial properties to cotton fabrics using alginate-quaternary ammonium complex nanoparticles. Carbohydrate polymers, 79(4), 1057-1062.
Li, P., et al. (2005). Synergistic antibacterial effects of β-lactam antibiotic combined with silver nanoparticles. Nanotechnology, 16(9), 1912.
Li, P., et al. (2011). A polycationic antimicrobial and biocompatible hydrogel with microbe membrane suctioning ability. Nature materials, 10(2), 149.
Lin J., et al. (2002). Bactericidal properties of flat surfaces and nanoparticles derivatized with alkylated polyethylenimines. Biotechnology Progress, 18(5), 1082-1086. (Only the abstracts are provided).
Lin, J., et al. (2003). Mechanism of bactericidal and fungicidal activities of textiles covalently modified with alkylated polyethylenimine. Biotechnology and Bioengineering, 83(2), 168-172. (Only abstract).
Majumdar, P., et al. (2009). Synthesis and antimicrobial activity of quaternary ammonium-functionalized POSS (Q-POSS) and polysiloxane coatings containing Q-POSS. Polymer, 50(5), 1124-1133.
Makvandi et al. (2015). Photocurable, antimicrobial quaternary ammonium-modified nanosilica. Journal of dental research, 94(10), 1401-1407.
Matalon, S., et al. (2003). Surface antibacterial properties of fissure sealants. Pediatric dentistry, 25(1), 43-48.
Melo, L. D., et al. (2010). Antimicrobial particles from cationic lipid and polyelectrolytes. Langmuir, 26(14), 12300-12306.
Nohr, R. S. et al. (1994). New biomaterials through surface segregation phenomenon: new quaternary ammonium compounds as antibacterial agents. Journal of Biomaterials Science, Polymer Edition, 5(6), 607-619. (Only abstract).
Novotná, E., et al. (2014). Synthesis and Biological Activity of Quaternary Ammonium Salt-Type Agents Containing Cholesterol and Terpenes. Archiv der Pharmazie, 347(6), 381-386.
Ono, M., et al. (2007). Surface properties of resin composite materials relative to biofilm formation. Dental materials journal, 26(5), 613-622.
Pu, Y., et al. (2016). Synthesis and antibacterial study of sulfobetaine/quaternary ammonium- modified star-shaped poly [2-(dimethylamino) ethyl methacrylate]-based copolymers with an inorganic core. Biomacromolecules, 18(1), 44-55.
Reinhardt, N., et al. (2015). Quaternary ammonium groups exposed at the surface of silica nanoparticles suitable for DNA complexation in the presence of cationic lipids. The Journal of Physical Chemistry B, 119(21), 6401-6411.
Richter, A. P., et al. (2015). An environmentally benign antimicrobial nanoparticle based on a silver-infused lignin core. Nature nanotechnology, 10(9), 817.

(56) References Cited

OTHER PUBLICATIONS

Rumbaugh, K. P., & Ahmad, I. (2014). Antibiofilm Agents. Springer Series on Biofilms, 8.
Sbordone, L., et al. (2003). Oral microbial biofilms and plaque-related diseases: microbial communities and their role in the shift from oral health to disease. Clinical oral investigations, 7(4), 181-188. (Only abstract).
Shalhav, M., et al. (1997). In vitro antibacterial activity of a glass ionomer endodontic sealer. Journal of endodontics, 23(10), 616-619.
Shvero, D. K., et al. (2010). Antibacterial effect of polyethyleneimine nanoparticles incorporated in provisional cements against *Streptococcus mutans*. Journal of Biomedical Materials Research Part B: Applied Biomaterials, 94(2), 367-371.
Shvero, D. K., et al. (2013). Towards antibacterial endodontic sealers using quaternary ammonium nanoparticles. International endodontic journal, 46(8), 747-754.
Shvero, D. K., et al. (2015). Characterisation of the antibacterial effect of polyethyleneimine nanoparticles in relation to particle distribution in resin composite. Journal of dentistry, 43(2), 287-294.
Siedenbiedel, F., et al. (2012). Antimicrobial polymers in solution and on surfaces: overview and functional principles. Polymers, 4(1), 46-71.
Song, J., et al. (2011). Bacterial adhesion inhibition of the quaternary ammonium functionalized silica nanoparticles. Colloids and Surfaces B: Biointerfaces, 82(2), 651-656.
Supplementary Search Report issued for EP Application No. 17 75 5952 dated Sep. 25, 2019.
Takei, et al. (1999). Investigation of the Structure of Surface Hydroxyl Groups on Silica Chemical Reaction and Molecular Adsorption Method. Journal of the Society of Powder Technology, Japan, 36(3), 179-184.
Weiss, E. I., et al. (1996). Assessment of antibacterial activity of endodontic sealers by a direct contact test. Dental Traumatology, 12(4), 179-184.
Wytrwal et al. (2014). "Synthesis of strong polycations with improved biological properties". Journal of Biomedical Materials Research Part A, 102(3), 721-731.
Xu, Q., et al. (2015). Polyurethane-coated silica particles with broad-spectrum antibacterial properties. Polymer Chemistry, 6(11), 2011-2022.
Yudovin-Farber, I., et al. (2008). Surface characterization and biocompatibility of restorative resin containing nanoparticles. Biomacromolecules, 9(11), 3044-3050.
Yudovin-Farber, I., et al. (2010). Antibacterial effect of composite resins containing quaternary ammonium polyethyleneimine nanoparticles. Journal of Nanoparticle Research, 12(2), 591-603.
Yudovin-Farber, I., et al. (2010). Quaternary ammonium polyethyleneimine: antibacterial activity. Journal of nanomaterials, 2010, 46.
Zaltsman, N., et al. (2017). Surface-modified nanoparticles as anti-biofilm filler for dental polymers. PloS one, 12(12), e0189397.
Chernov'yants MS, et al. "Synthesis and antimicrobial activity of poly(N-methyl-4-vinylpyridinium triiodide)". Translated from the Russian Khimiko-Farmatsevticheskii Zhurnal, vol. 44, No. 2, pp. 13-15, Feb. 2010.
Dong Hongchen et al. "Recyclable Antibacterial Magnetic Nanoparticles Grafted with Quaternized Poly (2-(dimethylamino) ethyl methacrylate) Brushes", Biomacromolecules, vol. 12 (4), Apr. 11, 2011, pp. 1305-1311.
Fuchs Andreas D. et al. "Contact-Active Antimicrobial Coatings Dervied from Aqueous Suspensions", Angew Chem Int Ed Engl Oct. 13, 2006;45(40):6759-62.
Guo F, et al. "A review of the synthesis and applications of polymer-nanoclay composites". Appl. Sci. 2018, vol. 8, issue 9, 1696. Published Sep. 19, 2018.
Hartlieb M, et al. "Antimicrobial Polymers: Mimicking Amino Acid Functionali ty, Sequence Control and Three-dimensional Structure of Host-defen se Peptides". Current medicinal chemistry. Jun. 1, 2017; 24(19):2115-40.
Indian Journal of Chemistry—Section B (IJC-B), 2014, vol. 53B, No. 7, p. 907-912, https://nopr.niscpr.res.in/handle/123456789/29157.
Kawabata NA, et al. "Removal of bacteria from water by adhesion to cross-linked poly(vinylpyridinium halide)". Appl. Environ. Microbiol. Jul. 1, 1983;46(1):203-10.
Kudaibergenov SE. "Polyampholytes: synthesis, characterization and application". Springer Science & Business Media; Published online Feb. 16, 2006.
Larikov et al. "Antimicrobial Surfaces using Covalently Bound Polyallylamine", Biomacromulecules vol. 15, 2014, pp. 169-176.
Martins AF, et al. "Antimicrobial activity of chitosan derivatives containing N-quaternized moieties in its backbone: A review". Int. J. Mol. Sci. 2014, 15, 20800-20832; Published Nov. 13, 2014.
Michailidis M, et al. "Modified mesoporous silica nanoparticles with a dual synergetic antibacterial effect". ACS applied materials & interfaces. Nov. 8, 2017; 9(44):38364-72.
Nataliya Kostenko et al. "A Synthetic Route to Quaternary Pyridinium Salt-Functionalized Silsesquioxanes" , International Journal of Polymer Science, vol. 38 (17), Jan. 1, 2012, pp. 3941-3949.
Reinhardt NME. "Chemical surface modification of silica nanoparticles for the labeling of DNA in lipoplexes". These Doctorale. Universite Sciences et Technologies—Bordeaux I. ubmitted on Oct. 2, 2015. Retrieved from the Internet: URL: <https://tel.archives-ouvertes.fr/tel-1208139/file/These_Reinhardt_Nora_2013.pdf.
Sarkyt Kudaibergenov; Werner Jaeger; Andre Laschewsky, "Polymeric Betaines: Synthesis, Characterization, and Application", Supramolecularpolymers, polymeric betains, oligomers; Advances in polymer science; ISSN 0065-3195, Berlin, Heidelberg, vol. 201, doi:10.1007/12_078, ISBN 978-3-540-31924-5, Jan. 1, 2006), pp. 157-224, URL: https://www.researchgate.net/publication/225434399_Polymeric_Betaines_Synthesis_Characterization_and_Application, XP009530005 [Y] 1, 2, 7, 9-15 *, lines 26-33, DOI: http://dx.doi.org/10.1007/12_078, Reference Date: 2002.
Savas LA, Hancer M. "Montmorillonite reinforced polymer nanocomposite antibacterial film". Applied Clay Science. May 1, 2015; 108:40-4.
Tu Q, et al. "Quantum dots modified with quaternized poly(dimethylaminoethyl methacrylate) for selective recognition and killing of bacteria over mammalian cells". Analyst. 2016;141(11):3328-3336.
Voo R, et al. "Properties of epoxy nanocomposite thin films prepared by spin coating technique". Journal of Plastic Film & Sheeting. Oct. 2011; 27(4):331-46.
Xometry, Polymer vs. Metal: what are the differences? tps://www.xometry.com/resources/materials/polymer-vs-metal/ Accessed Jul. 7, 2023, pp. 1-10.
Xu Q., et al. "Antimicrobial silica particles synthesized via ring-opening grafting of cationic amphiphilic cyclic carbonates: Effects of hyrodphobicity and structure". Polymer Chemistry. 2016;7(12):2192-2201. First published Feb. 29, 2016.
Yahiaoui Farida et al. "Development of Antimicrobial PCL/nanoclay Nanocomposite films with enhanced Mechanical and water vapor barrier properties for packaging applications", Polymer Bulletin, Springer, Heidelberg, DE, vol. 72 (2), Nov. 2, 2014, pp. 235-254.
Makvandi et al. (2018). "Antibacterial quaternary ammonium compounds in dental materials: A systematic review"; Apr. 2018, Dental Materials 34(6).

* cited by examiner

MICRO AND NANOPARTICULATE COMPOSITIONS COMPRISING ANTI-MICROBIALLY ACTIVE GROUPS

CROSS REFERENCE TO RELATED APPLICATIONS

This application is a Continuation Application of U.S. patent application Ser. No. 16/079,283 filed Aug. 23, 2018, which is a National Phase Application from International Application No. PCT/IL2017/050240 filed Feb. 26, 2017 which claims the benefit of International Application No. PCT/IL2016/050219 filed Feb. 25, 2016, the entire contents of which are hereby incorporated by reference herein.

FIELD OF THE INVENTION

The present invention relates to anti-microbially active particles, compositions comprising same, and use thereof for inhibiting bacterial growth on surfaces or devices. The present invention further discloses methods of making such anti-microbially active particles.

BACKGROUND OF THE INVENTION

The overwhelming diversity of bacteria in one individual's skin, gastro intestinal tract and oral cavity well documented, demonstrating a complex ecosystem anatomically and dynamically in which poly-microbial biofilms are the norm.

Biofilms formed on tissues outside and inside the organism are the major cause of infectious diseases. For example in the oral cavity, biofilm formed on dental hard or soft tissue are the major cause of caries and periodontal disease (Sbordone L., Bortolaia C., *Clin Oral Investig* 2003; 7:181-8). Bacterial biofilm forms on both natural and artificial surfaces.

Special attention is paid in recent years to artificial surfaces contacting organisms, as these surfaces lack the epithelial shedding, a major natural mechanism to combat biofilms, thus biofilm accumulation is becoming a major source of medical problems that may result in life threatening complications. Two major factors influence the susceptibility of a surface to accumulate bacteria; surface roughness and the surface-free energy which is a property of the material used. Surface roughness has a higher influence on the adhesion of bacteria than surface-free energy. In this context, artificial restorative materials typically have a higher surface roughness than natural surfaces, and therefore are more prone to bacterial accumulation. Therefore, the development of new materials that diminishes biofilm formation is a critical topic chronic infectious disease control, in various sites of the human body.

The ultimate goal of the development of materials with antibiofilm properties is to improve health and reduce disease occurrence. None of the existing medical devices can guarantee immediate and comprehensive elimination of biofilm or prevention of secondary infection.

For example, in order to sustain the oral defense, dental materials with the following antibiofilm properties are sought after: (1) inhibition of initial binding of microorganisms (2) preventing biofilm growth, (3) affecting microbial metabolism in the biofilm, (4) killing biofilm bacteria, and (5) detaching biofilm (Busscher H J, Rinastiti M, Siswomihardjo W, van der Mei H C., *J Dent Res,* 2010; 89:657-65; Marsh P D. *J Dent,* 2010; 38).

Resin-based composites are complex dental materials that consist of a hydrophobic resin matrix and less hydrophobic filler particles, which implies that a resin-based composite surface is never a homogeneous interface but rather one that produces matrix-rich and filler-poor areas, as well as matrix-poor and filler-rich areas (Ionescu A, Wutscher E, Brambilia E, Schneider-Feyrer S, Giessibl F J; Hahnel S., *Eur J Oral Sci* 2012; 120:458-65).

Biofilms on composites can cause surface deterioration. Polishing, as well as differences in the composition of the resin-based composite may have an impact on biofilm formation on the resin-based composite surface (Ono M. et al., *Dent Mater J,* 2007; 26:613-22). Surface degradation of resin composites driven by polishing leads to increased roughness, changes in micro hardness, and filler particle exposure upon exposure to biofilms in vitro. Furthermore, biofilms on composites can cause surface deterioration.

There still remains a need for and it would be advantageous to have an extended variety of anti-microbially active materials which are cost-effective, non-toxic and easy to apply to contaminated surfaces and devices, especially in dental products.

SUMMARY OF THE INVENTION

The present invention provides anti-microbially active functionalized particles, which can be embedded in a matrix to form compositions demonstrating a broad spectrum of anti-microbial activity. The compositions of the invention are preferably formulated for topical, on mucosal surfaces, skin surfaces, dental surfaces, wounds (chronic and acute) administration and can prevent the formation of biofilm oil surfaces and devices. Furthermore, the present invention provides versatile and cost-effective methodology for the preparation of the anti-microbially active particles of the invention.

The present invention is based on the surprising discovery that microparticles or nanoparticles comprising an inorganic or organic inert core, and anti-microbially active groups chemically bound to the core directly or via a linker at a surface density of at least one anti-microbially active group per 10 sq. nm, show a broad spectrum of anti-microbial activity when applied to or incorporated onto surfaces and devices on which the growth of such microbes may otherwise naturally take place. Such anti-microbial activity thus prevents biofilm formation. The particles generally include an inert core which can be made of an organic polymeric material or inorganic materials, as described herein and an anti-microbially active group comprising at least one hydrophobic group; wherein said particle is represented by the structure of formula 1 or salt thereof:

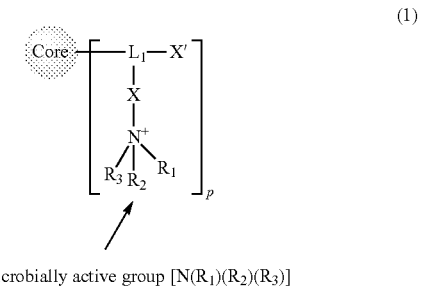

anti-microbially active group $[N(R_1)(R_2)(R_3)]$ wherein the core is an organic polymeric material, an inorganic material, zeolite, a metal or a metal oxide;
$L_1$ is a linker or a bond;
$R_1$ is alkyl, terpenoid, cycloalkyl, aryl, heterocycle, a conjugated alkyl, alkenyl, alkynyl or any combination thereof;
$R_2$ is alkyl, terpenoid, cycloalkyl, aryl, heterocycle, a conjugated alkyl, alkenyl, alkynyl or any combination thereof;
$R_3$ is nothing, hydrogen, alkyl, terpenoid moiety, cycloalkyl, aryl, heterocycle, a conjugated alkyl, alkenyl, alkynyl or any combination thereof;
X is a bond, alkyl, alkenyl, or alkynyl;
X' is nothing or hydrogen; and
p is the number of chains per one sq nm ($nm^2$) of the core surface, wherein the anti microbial active group is at a surface density of between 0.001-20 anti microbial active groups per one sq nm ($nm^2$) of the core surface of the particle;
wherein if $L_1$ and X are bonds, then the nitrogen is an integral part of the core;
wherein at least one of $R_1$, $R_2$, $R_3$ is hydrophobic.

In another embodiment, the particle is represented by formula 2 or salt thereof:

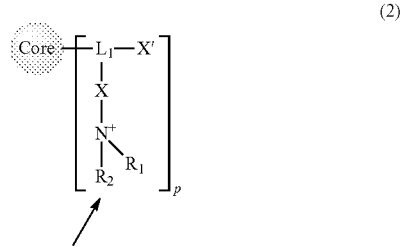

(2)

anti-microbially active group [N($R_1$)($R_2$)]

wherein $R_1$ and $R_2$ are as described for structure (1).

In another embodiment, the particle is represented by formula 3 or salts thereof:

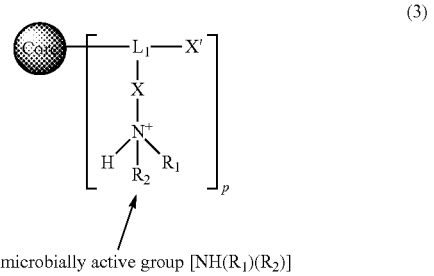

(3)

anti-microbially active group [NH($R_1$)($R_2$)]

wherein $R_1$ and $R_2$ are as described for structure (1).

The particles of the present invention demonstrate enhanced anti-bacterial activity originating from the presence of closely packed anti-bacterial groups on a given particle's surface. This effect yields a high local concentration of active functional groups (at least one anti-microbially active group per 10 sq. nm of the core surface, preferably at least one anti-microbially active group per 1 sq. nm of the core surface), which results in high effective concentration of the functionalized particles and enables the use of a relatively small amount of particles to achieve effective bacterial annihilation.

In one embodiment, this invention provides a positively charged particle comprising:
(i) an inorganic core; and
(ii) anti-microbially active groups chemically bound to the core at a surface density of at least one anti-microbially active group per 10 sq. nm,
wherein the anti-microbially active group is a quaternary ammonium group, the nitrogen atom of each quaternary ammonium group having one bond to an alkyl group having from 4 to 24 carbon atoms, and a remainder of bonds each being to an alkyl group having from 1 to 3 carbon atoms.

In one embodiment, this invention provides a positively charged particle comprising:
(i) an inorganic core selected from silicate ($SiO_4^-$), surface activated metal metal oxide and Zeolite; and
(ii) anti-microbially active groups chemically bound to the core at a surface density of at least one anti-microbially active group per 10 sq. nm of the core surface,
wherein the anti-microbially active group is a quaternary ammonium group, the nitrogen atom of each quaternary ammonium group having one bond to an alkyl group having from 4 to 24 carbon atoms, and a remainder of bonds each being to an alkyl group having from 1 to 3 carbon atoms.

In one embodiment, this invention provides a composition comprising a liquid or solid matrix embedding a plurality of particles of this invention, wherein the particles are embedded in the matrix through covalent or non-covalent interactions.

In one embodiment, this invention provides a pharmaceutical composition comprising the particles of this invention.

In one embodiment, this invention provides a method for inhibiting or preventing biofilm formation, comprising applying onto a susceptible or infected surface or a medical device a particle of this invention or combination of particles, or a pharmaceutical composition comprising such particle(s).

In another embodiment, the present invention provides a particle or a pharmaceutical composition comprising such particle as described above for use in inhibiting or preventing a biofilm formation.

In one embodiment, this invention provides a method for inhibition of bacteria, the method comprising the step of contacting the bacteria with the particle or combination of particles of this invention, or a composition comprising such particle or combination of particles. In some embodiments, the anti-bacterial compositions of the present invention affect annihilation of at least about 99% of the contacted bacteria, preferably, at least about 99.99% of the contacted bacteria.

It was further surprisingly discovered that these microparticles and nanoparticles maintain high anti-microbial properties over time without leaching out and with no alteration of the properties of the hosting matrix.

The particles of the present invention demonstrate enhanced anti-bacterial activity originating from the presence of closely packed anti-bacterial groups on a given particle's surface. This effect yields a high local concentration of active functional groups (at least one anti-microbially active group per 10 sq. nm of the core surface, preferably at least one anti-microbially active group per 1 sq. nm of the core surface), which results in high effective concentration of the functionalized particles and enables the use of a relatively small amount of particles to achieve effective bacterial annihilation.

In one embodiment, this invention provides a packaging composition comprising a thermoplastic polymer and a particle of this invention embedded therein. In another embodiment, the packaging composition comprises a mixture of two or more different particles of this invention. In another embodiment, the packaging is for use for packaging of food, beverage, pharmaceutical ingredients, medical devices, surgical equipment before operation, pre operation equipment, cosmetics, sterilized equipment/materials.

Further embodiments and the full scope of applicability of the present invention will become apparent from the detailed description given hereinafter. However, it should be understood that the detailed description and examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 9A) an image of the cylindrical specimens; FIG. 9B) compressive strength test of modified and unmodified specimens.

FIG. 10A) anti-microbial activity against the Graham positive bacteria *E. faecalis*. The results were compared with the natural growth of *E. faecalis*. FIG. 10B) anti-microbial activity against the Graham positive bacteria *S. aureus*. The results were compared with the natural growth of *S. aureus*.

FIG. 14A) by first utilizing reductive amination to achieve tertiary amine, followed by an alkylation reaction, FIG. 14B) by stepwise alkylation reactions; and FIG. 14C) by reacting a linker functionalized with a leaving group (e.g., Cl or other halogen) with tertiary amine. $R^1$ and $R^2$ represent $C_1$-$C_3$ alkyls such as methyl, ethyl, propyl or isopropyl. $R^1$ and $R^2$ may be different or the same group. Y represents any leaving group, for example Cl, Br or I, or a sulfonate (e.g., mesyl, tosyl).

DETAILED DESCRIPTION OF THE INVENTION

Particles

Figure 1:
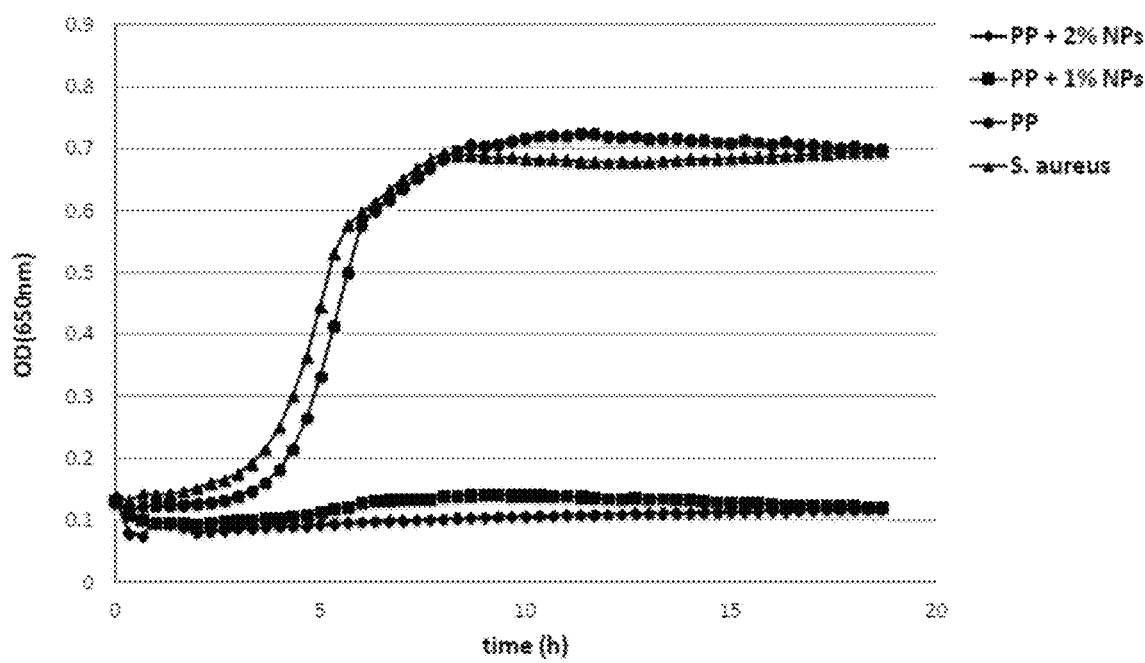
FIG. 1: depicts the anti-microbial activity of a polypropylene matrix without (PP) and with 1% wt/wt (PP+1% NPs) or 2% wt/wt (PP+2% NPs) silica particles functionalized with dimethyl octyl ammonium groups, against the Graham positive bacteria *Staphylococcus aureus* (*S. aureus*). The embedded particles were 186 nm in diameter on average, and the results were compared with the natural growth of *S. aureus*.

The present invention provides anti-microbially active functionalized micro or nanoparticles, and compositions thereof demonstrating a broad spectrum of anti-microbial activity. The particles are positively charged particles including an inert core which can be made of an organic polymeric material, or an inorganic material, as described herein and an anti microbial group which is attached to the core directly or indirectly.

In one embodiment, the anti microbial active group is a protonated tertiary amine or a quaternary ammonium. In another embodiment, the anti microbial active group is represented by the following formula:

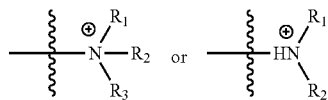

wherein:

$R_1$ is alkyl, terpenoid, cycloalkyl, aryl, heterocycle, a conjugated alkyl, alkenyl, alkynyl or any combination thereof;

$R_2$ is alkyl, terpenoid, cycloalkyl, aryl, heterocycle, a conjugated alkyl, alkenyl, alkynyl or any combination thereof;

$R_3$ is nothing, hydrogen, alkyl, terpenoid moiety, cycloalkyl, aryl, heterocycle, a conjugated alkyl, alkenyl, alkynyl or any combination thereof;

wherein at least one of $R_1$, $R_2$ or $R_3$ is hydrophobic.

In some embodiments, the particle of this invention is represented by the structure of formulas 1-3 or salt thereof:

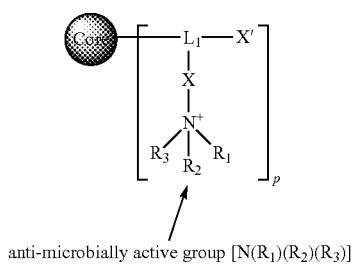

(1)

anti-microbially active group [$N(R_1)(R_2)(R_3)$]

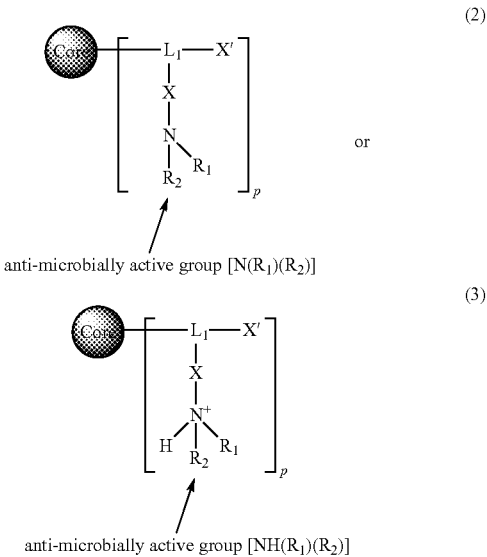

anti-microbially active group [$N(R_1)(R_2)$]

anti-microbially active group [$NH(R_1)(R_2)$]

wherein, the core is an organic polymeric material, an inorganic material, a metal, zeolite or a metal oxide;

$L_1$ is a linker or a bond;

$R_1$ is alkyl, terpenoid, cycloalkyl, aryl, heterocycle, a conjugated alkyl, alkenyl, alkynyl or any combination thereof;

$R_2$ is alkyl, terpenoid, cycloalkyl, aryl, heterocycle, a conjugated alkyl, alkenyl, alkynyl or any combination thereof;

$R_3$ is nothing, hydrogen, alkyl, terpenoid moiety, cycloalkyl, aryl, heterocycle, a conjugated alkyl, alkenyl, alkynyl or any combination thereof;

X is a bond, alkyl, alkenyl, or alkynyl;

X' is nothing or hydrogen; and p is the number of chains per one sq nm of the core surface, wherein the anti microbial active group is at a surface density of between 0.001-20 anti-microbial active groups per one sq nm of the core surface of the particle; wherein if $L_1$ and X are bonds, then the nitrogen is an integral part of the core;

wherein at least one of $R_1$, $R_2$, $R_3$ is hydrophobic.

In one embodiment, the particle of this invention has a surface density of the anti microbial group on the surface of the core of at least 1 anti microbial group per 10 sq nm. In another embodiment at least 1 anti microbial group per 1 sq nm of the core surface. In another embodiment between 0.001-20 anti microbial groups per sq nm of the core surface. In another embodiment between 0.001-17 anti microbial groups per sq nm of the core surface. In another embodiment between 0.001-15 anti microbial groups per sq nm of the core surface. In another embodiment between 0.001-10 anti microbial groups per sq nm of the core surface. In another embodiment between 0.001-4 anti microbial groups per sq nm of the core surface. In another embodiment between 0.001-1 anti microbial groups per sq nm of the core surface. In another embodiment between 1-4 anti microbial groups per sq nm of the core surface. In another embodiment between 1-6 anti microbial groups per sq nm of the core surface. In another embodiment between 1-20 anti microbial groups per sq nm of the core surface. In another embodiment between 1-10 anti microbial groups per sq nm of the core surface. In another embodiment between 1-15 anti microbial groups per sq nm of the core surface.

In another embodiment, the particle of structures (1) to (3) has an inorganic core. In another embodiment, the particle of structure (1) to (3) has an organic core. In another embodiment, the organic core is a polymeric organic core. In another embodiment, the core is inert. In one embodiment, the particles of this invention represented by structures (1)-(3) comprise an anti-microbial active group of $-^+N(R_1)(R_2)(R_3)$, $-^+NR(R_1)(R_2)$ or $-N(R_1)(R_2)$. In one embodiment $R_1$, $R_2$ and $R_3$ are independently alkyl, terpenoid, cycloalkyl, aryl, heterocycle a conjugated alkyl, alkenyl, alkynyl or any combination thereof. In another embodiment, $R_1$, $R_1$ and $R_3$ are independently an alkyl. In another embodiment, $R_1$, $R_2$ and $R_3$ are independently a terpenoid. In another embodiment, $R_1$, $R_2$ and $R_3$ are independently a cycloalkyl. In another embodiment, $R_1$, $R_2$ and $R_3$ are independently an aryl. In another embodiment, $R_1$, $R_2$ and $R_3$ are independently a heterocycle. In another embodiment, $R_1$, $R_2$ and $R_3$ are independently a conjugated alkyl. In another embodiment, $R_1$, $R_2$ and $R_3$ are independently an alkenyl. In another embodiment, $R_1$, $R_2$ and $R_3$ are independently an alkynyl or any combination thereof alkynyl. In another embodiment, $R_3$ is nothing. In another embodiment, $R_3$ is hydrogen. In another embodiment at least one on $R_1$, $R_2$ and $R_3$ is hydrophobic alkyl, terpenoid, cycloalkyl, aryl, heterocycle, a conjugated alkyl, alkenyl, alkynyl or any combination thereof.

As used herein, the term "alkyl" or "alkylene" can be any linear- or branched-chain alkyl group containing up to about 24 carbons unless otherwise specified. In one embodiment, an alkyl includes $C_1$-$C_3$ carbons. In one embodiment, an alkyl includes $C_1$-$C_4$ carbons. In one embodiment, an alkyl includes $C_1$-$C_5$ carbons. In another embodiment, an alkyl includes $C_1$-$C_6$ carbons. In another embodiment, an alkyl includes $C_1$-$C_8$ carbons. In another embodiment, an alkyl includes $C_1$-$C_{10}$ carbons. In another embodiment, an alkyl includes $C_1$-$C_{12}$ carbons. In another embodiment, an alkyl includes $C_4$-$C_8$ carbons. In another embodiment, an alkyl include $C_4$-$C_{18}$ carbons. In another embodiment, an alkyl include $C_4$-$C_{24}$ carbons. In another embodiment, an alkyl includes $C_1$-$C_{18}$ carbons. In another embodiment, an alkyl includes $C_2$-$C_{18}$ carbons. In another embodiment, branched alkyl is an alkyl substituted by alkyl side chains of 1 to 5 carbons. In one embodiment, the alkyl group may be unsubstituted. In another embodiment, the alkyl group may be substituted by a halogen, haloalkyl, hydroxyl, alkoxy, carbonyl, amino, alkylamido, dialkylamido, cyano, nitro, $CO_2H$, amino, alkylamino, dialkylamino, carboxyl, thio and/or thioalkyl. In another embodiment hydrophobic alkyl refers to alkyl having at least four carbons. In another embodiment hydrophobic alkyl refers to a $C_4$-$C_8$ alkyl.

A "conjugated alkyl" refers to alkyl as defined above having alternative single and double or triple bonds. In another embodiment hydrophobic conjugated alkyl refers to conjugated alkyl having at least four carbons. In another embodiment hydrophobic conjugated alkyl refers to a conjugated alkyl having a $C_4$-$C_{18}$ alkyl.

As used herein, the term "aryl" refers to any aromatic ring that is directly bonded to another group and can be either substituted or unsubstituted. The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc. Substitutions include but are not limited to: F, Cl, Br, I, $C_1$-$C_5$ linear or branched alkyl, $C_1$-$C_5$ linear or branched haloalkyl, $C_1$-$C_5$ linear or branched alkoxy, $C_1$-$C_5$ linear or branched haloalkoxy, $CF_3$, CN, $NO_2$, $-CH_2CN$, $NH_2$, N(alkyl)$_2$, hydroxyl, $-OC(O)CF_3$, $-OCH_2Ph$, $-NHCO$-alkyl, COOH, $-C(O)Ph$, $C(O)O$-alkyl, $C(O)H$, or $-C(O)NH_2$. In another embodiment hydrophobic aryl refers to aryl having at least six carbons.

The term "alkenyl" refers to a substance that includes at least two carbon atoms and at least one double bond. In one embodiment, the alkenyl has 2-7 carbon atoms. In another embodiment, the alkenyl has 2-12 carbon atoms. In another embodiment, the alkenyl has 2-10 carbon atoms. In another embodiment, the alkenyl has 3-6 carbon atoms. In another embodiment, the alkenyl has 2-4 carbon atoms. In another embodiment, the alkenyl has 4-8 carbon atoms. In another embodiment hydrophobic alkenyl refers to alkenyl having at least four carbons. In another embodiment hydrophobic Amyl refers to a $C_4$-$C_8$ alkenyl.

The term "alkynyl" refers to a substance that includes at least two carbon atoms and at least one triple bond. In one embodiment, the alkynyl has 2-7 carbon atoms. In another embodiment, the alkynyl has 2-12 carbon atoms. In another embodiment, the alkynyl has 2-10 carbon atoms. In another embodiment, the alkynyl has 3-6 carbon atoms. In another embodiment, the alkynyl has 2-4 carbon atoms. In another embodiment, the alkynyl has 3-6 carbon atoms. In another embodiment, the alkynyl has 4-8 carbon atoms. In another embodiment hydrophobic alkynyl refers to alkynyl having at least four carbons. In another embodiment hydrophobic alkynyl refers to a $C_4$-$C_8$ alkenyl.

The term "alkoxy" refers in one embodiment to an alky as defined above bonded to an oxygen. Non limiting examples of alkoxy groups include: methoxy, ethoxy and isopropoxy.

A "cycloalkyl" group refers, in one embodiment, to a ring structure comprising carbon atoms as ring atoms, which may be either saturated or unsaturated, substituted or unsubstituted. In another embodiment the cycloalkyl is a 3-12 membered ring. In another embodiment the cycloalkyl is a 6 membered ring. In another embodiment the cycloalkyl is a 5-7 membered ring. In another embodiment the cycloalkyl is a 3-8 membered ring. In another embodiment, the cycloalkyl group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the cycloalkyl ring may be fused to another saturated or unsaturated cycloalkyl or heterocyclic 3-8 membered ring. In another embodiment, the cycloalkyl ring is a saturated ring. In another embodiment, the cycloalkyl ring is an unsaturated ring. Non limiting examples of a cycloalkyl group comprise cyclohexyl, cyclohexenyl, cyclopropyl, cyclopropenyl, cyclopentyl, cyclopentenyl, cyclobutyl, cyclobutenyl, cyclooctyl, cyclooctadienyl (COD), cycloctaene (COE) etc. In another embodiment hydrophobic cycloalkyl refers to a cycloalkyl having at least six carbons.

A "heterocycle" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 3-8 membered ring. In another embodiment, the heterocycle group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. Non limiting examples of a heterocyclic rings comprise pyridine, piperidine, morpholine, piperazine, thiophene, pyrrole, benzodioxole, or indole. In another embodiment hydrophobic heterocyclic group refers to a heterocycle having at least six carbons.

In one embodiment, at least one of $R_1$, $R_2$ and $R_3$ of structure (1) is hydrophobic. In one embodiment, at least one of $R_1$ and $R_2$ of structures (2) and (3) is hydrophobic.

The term "hydrophobic" refers to an alkyl, alkenyl or alkynyl having at least four carbons, or the term hydrophobic refers to terpenoid, to cycloalkyl, aryl or heterocycle having at least six carbons. Each possibility represents a separate embodiment of the present invention In another embodiment, at least one of $R_1$, $R_2$ and $R_3$ of structure (1) is a $C_4$-$C_{24}$ alkyl, $C_4$-$C_{24}$ alkenyl, $C_4$-$C_{24}$ alkynyl or a terpenoid. In one embodiment, at least one of $R_1$ and $R_2$ of structures (2) and (3) is a $C_4$-$C_{24}$ alkyl, $C_4$-$C_{24}$ alkenyl, $C_4$-$C_{24}$ alkynyl or a terpenoid. Each possibility represents a separate embodiment of the present invention.

In one embodiment, $R_1$ of structures (1) to (3) is a terpenoid. In another embodiment, $R_1$ is a terpenoid and $R_2$ is a $C_1$-$C_4$ alkyl. In another embodiment, the core is an organic polymeric core, $R_3$ is nothing and $R_1$ is a terpenoid. In another embodiment, the core is an organic polymeric core, $R_3$ is hydrogen and $R_1$ is a terpenoid. In another embodiment, the core is an inorganic core, $R_3$ is nothing and $R_1$ is a terpenoid. In another embodiment, the core is an inorganic core, $R_3$ is hydrogen and $R_1$ is a terpenoid. In another embodiment, the core is an inorganic core, $R_3$ is $C_1$-$C_{24}$ alkyl, terpenoid, cycloalkyl, aryl, heterocycle, a conjugated $C_1$-$C_{24}$ alkyl, $C_1$-$C_{24}$ alkenyl, $C_1$-$C_{24}$ alkynyl or any combination thereof and $R_1$ is a terpenoid.

In one embodiment "p" of structures (1) to (3) is defines the surface density of the anti microbial active group on the core surface. In another embodiment "p" is, between 0.001-20 anti microbial active groups per 1 sq nm of the core surface. In another embodiment "p" is between 0.001-17 anti microbial groups per sq nm of the core surface. In another embodiment "p" is between 0.001-15 anti microbial groups per sq nm of the core surface. In another embodiment "p" is between 0.001-10 anti microbial groups per sq nm of the core surface. In another embodiment "p" is between 0.001-4 anti microbial groups per sq nm of the core surface. In another embodiment "p" is between 0.001-1 anti microbial groups per sq nm of the core surface. In another embodiment, "p" is between 1-4 anti microbial groups per sq nm of the core surface. In another embodiment "p" is between 1-6 anti microbial groups per sq nm of the core surface. In another embodiment "p" is between 1-20 anti microbial groups per sq nm of the core surface. In another embodiment "p" is between 1-10 anti microbial groups per sq nm of the core surface. In another embodiment "p" is between 1-15 anti microbial groups per sq nm of the core surface.

In one embodiment, the anti-microbially active group may be selected from: (a) a tertiary amine (i.e. $R_3$ is nothing) or tertiary ammonium (i.e. $R_3$ is hydrogen) comprising at least one terpenoid moiety (b) a quaternary ammonium group comprising at least one terpenoid moiety (c) a quaternary ammonium group, comprising at least one alkyl group having from 4 to 24 carbon atoms; and (d) a tertiary amine (i.e. $R_3$ is nothing) or tertiary ammonium (i.e. $R_3$ is hydrogen) comprising at least one alkyl group having from 4 to 24 carbon atoms. Each possibility represents a separate embodiment of the invention.

In one embodiment, the anti-microbially active group may be selected from: (a) a tertiary amine (i.e. $R_3$ is nothing) or tertiary ammonium (i.e. $R_3$ is hydrogen) comprising at least one terpenoid moiety and optionally an alkyl group having from 1 to 4 carbon atoms, or a salt of said amine (i.e. $R_1$ and $R_2$ are terpenoid moieties or $R_1$ is a terpenoid moiety and $R_2$ is a $C_1$-$C_4$ alkyl); (b) a quaternary ammonium group comprising at least one terpenoid moiety and optionally one or more alkyl groups having from 1 to 4 carbon atoms (i.e. $R_1$, $R_2$ and $R_3$ are terpenoid moieties; or $R_1$ and $R_2$ are terpenoid moieties and $R_3$ is $C_1$-$C_4$ alkyl or $R_1$ and $R_3$ are terpenoid moieties and $R_2$ is $C_1$-$C_4$ alkyl; or $R_1$ is a terpenoid moiety and $R_2$ and $R_3$ are $C_1$-$C_4$ alkyl); (c) a quaternary ammonium group, comprising at least one alkyl group having from 4 to 24 carbon atoms, and a remainder of bonds each being to an alkyl group having from 1 to 3 carbon atoms (i.e. $R_1$, $R_2$ and $R_3$ are a $C_4$-$C_{24}$ alkyl or $R_1$ and $R_2$ are $C_4$-$C_{24}$ alkyl and $R_3$ is $C_1$-$C_3$ alkyl or $R_1$ and $R_3$ are $C_4$-$C_{24}$ alkyl and $R_2$ is $C_1$-$C_3$ alkyl; or $R_1$ is a $C_4$-$C_{24}$ alkyl and $R_2$ and $R_3$ are $C_1$-$C_3$ alkyl); and (d) a tertiary amine (i.e. $R_3$ is nothing) or tertiary ammonium (i.e. $R_3$ is hydrogen) comprising at least one alkyl group having from 4 to 24 carbon atoms and the remainder of bonds each being to an alkyl group having from 1 to 3 carbon atoms (i.e. $R_1$ and $R_2$ are a $C_4$-$C_{24}$ alkyl; or $R_1$ is a $C_4$-$C_{24}$ alkyl and $R_2$ is a $C_1$-$C_3$ alkyl). Each possibility represents a separate embodiment of the invention.

In one embodiment, the particles of this invention represented by structures (1)-(3) comprise an anti-microbial active group and an inert core, wherein the anti-microbial active group and the core are linked directly of indirectly. In another embodiment, the anti-microbial active group and the core are linked indirectly via $L_1$-X. In another embodiment $L_1$ is a linker or a bond. In another embodiment, $L_1$ is a bond. In another embodiment, $L_1$ is a linker.

In some embodiments $L_1$ is a linker comprising an alkyl, alkenyl, alkyl phosphate, alkyl siloxanes, epoxy, acylhalide, glycidyl, carboxylate, anhydrides, or any combination thereof, wherein the functional group is attached to the core. Each possibility represents a separate embodiment of the present invention.

In another embodiment, the linker is a C1 to C18 alkylene substituted with at least one carboxyl moiety, wherein the carboxyl end is attached to the core. This linker may be derived from a C1 to C18 alkylene substituted with at least one carboxyl moiety and having an amino end which is modified to antibacterial active group $[N(R_1)(R_2)(R_3)]$ (defined in formula 1). This linker may be derived from an amino acid of natural or synthetic source having a chain length of between 2 and 18 carbon atoms (polypeptide), or an acyl halide of said amino acid. Non-limiting examples for such amino acids are 18-amino octadecanoic acid and 18-amino stearic acid;

In another embodiment, the linker is a C1 to C18 alkylene. This linker may be derived from a di-halo alkylene, which is functionalized at each end with the core and anti-microbially active group, respectively, by replacement of the halogen moiety to a functional group that will bind to the core and replacement of the halogen moiety to obtain $[N(R_1)(R_2)(R_3)]$ (defined in formula 1).

In another embodiment, the linker is an aromatic group derived from non limiting examples of 4,4-biphenol, dibenzoic acid, dibenzoic halides, dibenzoic sulphonates, terephthalic acid, terephthalic halides, and terephthalic sulphonates. This linker is functionalized with the core and anti-microbially active group, respectively, through the functional group thereof (i.e., hydroxyl, carboxy or sulfonate). In another embodiment, this linker is attached to the core at one end and is modified at the other end to anti-microbially active group $N(R_1)(R_2)(R_3)$.

In another embodiment, the linker is represented by the structure of formula IA:

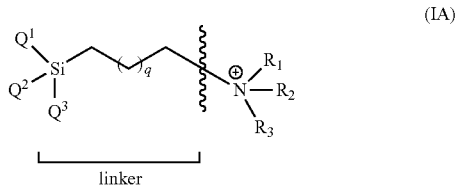

wherein
$Q^1$, $Q^2$ and $Q^3$ are independently selected from the group consisting of alkoxy, methyl, ethyl, hydrogen, sulfonate and halide, wherein at least one of $Q^1$, $Q^2$ and $Q^3$ is selected from ethoxy, methoxy, sulfonate (e.g., mesyl, tosyl) and halide;
q is an integer between 1 and 16;
$R_1$ and $R_1$ are independently linear or branched alkyl, terpenoid, cycloalkyl, aryl, heterocycle, a conjugated alkyl, alkenyl, alkynyl or any combination thereof; and
$R_3$ is nothing, hydrogen, linear or branched alkyl, terpenoid, cycloalkyl, aryl, heterocycle, a conjugated alkyl, alkenyl, alkynyl or any combination thereof;
wherein said linker is chemically bound to the core surface through the silicon side.

The particles of the present invention demonstrate an enhanced anti-bacterial activity originating from the presence of closely packed anti-bacterial groups on a given core's surface, as well as high density of particles packed on the surface of a host matrix. The surface density of the anti-microbial group results in high effective concentration promoting anti-bacterial inhibitory effect. According to the principles of the present invention, high surface density dictates high anti-microbial efficiency.

The anti-microbially active groups of the present invention are chemically bound to the core at a surface density of at least one anti-microbially active group per 10 sq. nm of the core surface. In one preferred embodiment, the particle includes at least 1 anti-microbially active quaternary ammonium group per sq. nm of core surface. In another embodiment at least 1 anti microbial group per 1 sq nm of the core surface. In another embodiment between 0.001-20 anti microbial groups per sq nm of the core surface. In another embodiment between 0.001-10 anti microbial groups per sq nm of the core surface. In another embodiment between 0.001-4 anti microbial groups per sq nm of the core surface. In another embodiment between 0.001-1 anti microbial groups per sq nm of the core surface. In another embodiment between 1-4 anti microbial groups per sq nm of the core surface. In another embodiment between 1-6 anti microbial groups per sq nm of the core surface. In another embodiment between 1-20 anti microbial groups per sq nm of the core surface. In another embodiment between 1-10 anti microbial groups per sq nm of the core surface. In another embodiment between 1-15 anti microbial groups per sq nm of the core surface.

The term "nanoparticle" as used herein refers to a particle having a diameter of less than about 1,000 nm. The term "microparticle" as used herein refers to a particle having a diameter of about 1,000 nm or larger.

The particles of the present invention are characterized by having a diameter between about 5 to about 100,000 nm, and thus encompass both nanoparticulate and microparticulate compositions. Preferred are particles between about 10 to about 50,000 nm. In other embodiments, the particles are more than 1,000 nm in diameter. In other embodiments, the particles are more than 10,000 nm in diameter. In other embodiment, the particles are between 1,000 and 50,000 nm in diameter. In other embodiments, the particles are between 5 and 250 nm in diameter. In other embodiment, the particles are between 5 and 500 nm in diameter. In another embodiment, the particles are between 5 and 1000 nm in diameter. It is apparent to a person of skill in the art that other particles size ranges are applicable and are encompassed within the scope of the present invention.

Anti-Microbially Active Groups Comprising Terpenoid Groups

In one embodiment, the anti-microbially active group of the present invention contains at least one terpenoid group, and is selected from: (a) a tertiary amine ($R_3$ is nothing) or tertiary ammonium ($R_3$ is H) comprising at least one terpenoid moiety; and (b) a quaternary ammonium group comprising at least one terpenoid moiety.

In one embodiment, the anti-microbially active group of the present invention contains at least one terpenoid group, and is selected from: (a) a tertiary amine ($R_3$ is nothing) or tertiary ammonium ($R_3$ is H) comprising at least one terpenoid moiety and optionally an alkyl group having from 1 to 4 carbon atoms, or a salt of said amine/ammonium (i.e. $R_1$ and $R_2$ are terpenoid moieties or $R_1$ is a terpenoid moiety and $R_2$ is a $C_1$-$C_4$ alkyl); (b) a quaternary ammonium group comprising at least one terpenoid moiety and optionally one or more alkyl groups having from 1 to 4 carbon atoms (i.e. $R_1$, $R_2$ and $R_3$ are terpenoid moieties; or $R_1$ and $R_2$ are terpenoid moieties and $R_3$ is $C_1$-$C_4$ alkyl or $R_1$ and $R_3$ are terpenoid moieties and $R_2$ is $C_1$-$C_4$ alkyl; or $R_1$ is a terpenoid moiety and $R_2$ and $R_3$ are alkyl).

In some embodiments, the anti-microbially active group is selected from: (a) a tertiary amine ($R_3$ is nothing) or tertiary ammonium ($R_3$ is H), wherein the nitrogen atom of each tertiary amine/ammonium having at least one bond to the core (directly (i.e. in structures 1-3: X is a bond; $L_1$ is a bond; and X' is nothing) or via a linker), one bond to a terpenoid moiety and optionally the remaining bond to an alkyl group having from 1 to 4 carbon atoms or a salt of said tertiary amine (i.e. $R_1$ is a terpenoid moiety and $R_2$ is a $C_1$-$C_4$ alkyl); (b) a tertiary amine ($R_3$ is nothing), or tertiary ammonium ($R_3$ is H), the nitrogen atom of each tertiary amine/ammonium having one bond to the core (directly (i.e. in formulas 1-3: X is a bond; $L_1$ is a bond; and X' is nothing) or via a linker), and two bonds to terpenoid moieties which may be the same or different from each other, or a salt of said tertiary amine (i.e. $R_1$ and $R_2$ are terpenoid moieties); (c) a quaternary ammonium group the nitrogen atom of each quaternary ammonium group having at least one bond to the core directly (i.e. in formulas 1-3: X is a bond; $L_1$ is a bond; and X' is nothing) or via a linker, one or two bonds to terpenoid moieties which may be the same or different from each other, and optionally remaining bond to an alkyl group having from 1 to 4 carbon atoms (i.e. $R_1$ and $R_2$ are terpenoid moieties and R$_3$ is C$_1$-C$_4$ alkyl or R$_1$ and R$_3$ are terpenoid moieties and R$_2$ is C$_1$-C$_4$ alkyl; or R$_1$ is a terpenoid moiety and R$_2$ and R$_3$ are C$_1$-C$_4$ alkyl); Each possibility represents a separate embodiment of the present invention.

The term "terpenoid", also known as "isoprenoid" refers to a large class of naturally occurring compounds that are derived from five-carbon isoprene units.

In one embodiment, the at least one terpenoid moiety is a cinnamyl group derived from cinnamaldehyde, cinnamic acid, curcumin, viscidone or cinnamyl alcohol. In another embodiment, the at least one terpenoid moiety is a bornyl group derived from camphor, bornyl halide or bornyl alcohol. In another embodiment, the at least one terpenoid moiety is derived from citral. In another embodiment, the at least one terpenoid moiety is derived from perillaldehyde. Each possibility represents a separate embodiment of the present invention.

Cinnamaldehyde is a natural aldehyde extracted from the genus *Cinnamomum*. It is known for its low toxicity and its effectiveness against various bacteria and fungi.

Camphor is found in the wood of the camphor laurel (*Cinnamomum camphora*), and also of the kapur tree. It also occurs in some other related trees in the laurel family, for example *Ocotea usambarensis*, as well as other natural sources. Camphor can also be synthetically produced from oil of turpentine.

Citral, or 3,7-dimethyl-2,6-octadienal or lemonal, is a mixture of two diastereomeric terpenoids. The two compounds are double bond isomers. The E-isomer is known as geranial or citral A. The Z-isomer is known as neral or citral B. Citral is known to have anti-bacterial activity.

Perillaldehyde, also known as perilla aldehyde, is a natural terpenoid found most in the annual herb perilla, as well as in a wide variety of other plants and essential oils.

Other examples of terpenoids include, but are not limited to: curcuminoids found in turmeric and mustard seed, and citronellal found in Cymbopogon (lemon grass). Each possibility represents a separate embodiment of the present invention.

In accordance with the above embodiment, the one anti-microbially active terpenoid moiety is selected from the group consisting of:

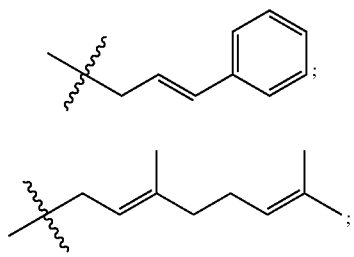

(i)

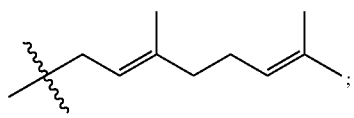

(ii)

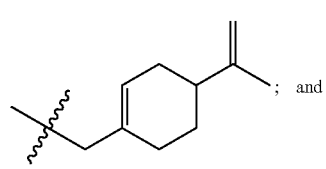

(iii) ; and

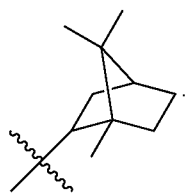

(iv)

Each possibility represents a separate embodiment of the present invention.

Non-limiting examples of functional anti-microbially active tertiary amine groups or its protonated form in accordance with the principles of the present invention are:

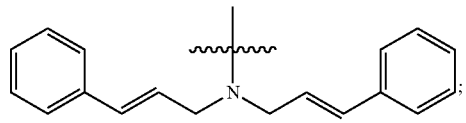

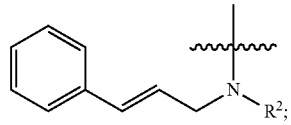

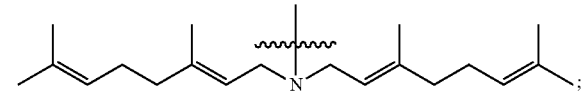

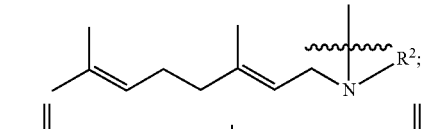

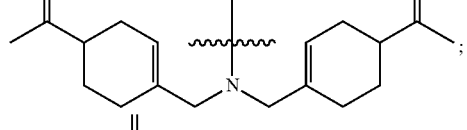

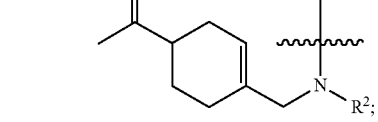

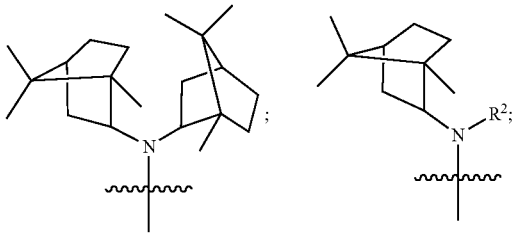

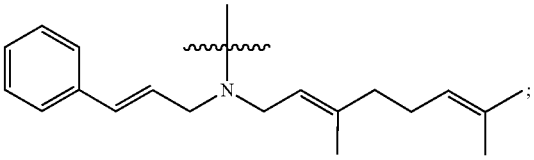

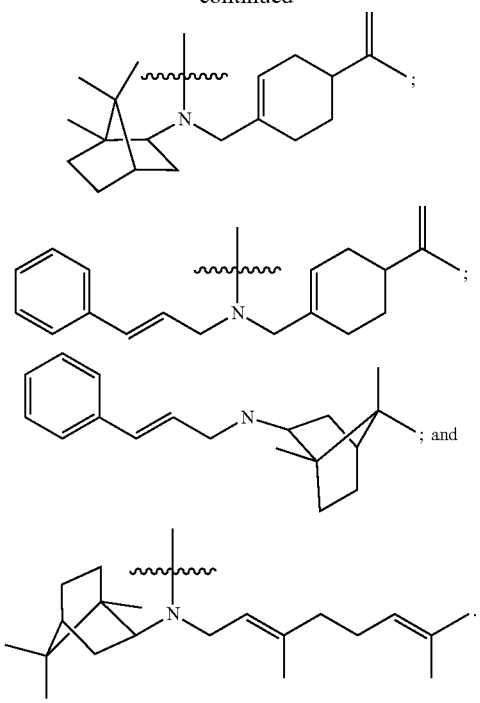
wherein R² is alkyl, terpenoid, cycloalkyl, aryl, heterocycle, a conjugated alkyl, alkenyl, alkynyl or any combination thereof.
Non-limiting examples of anti-microbially active quaternary ammonium groups in accordance with the principles of the present invention are:
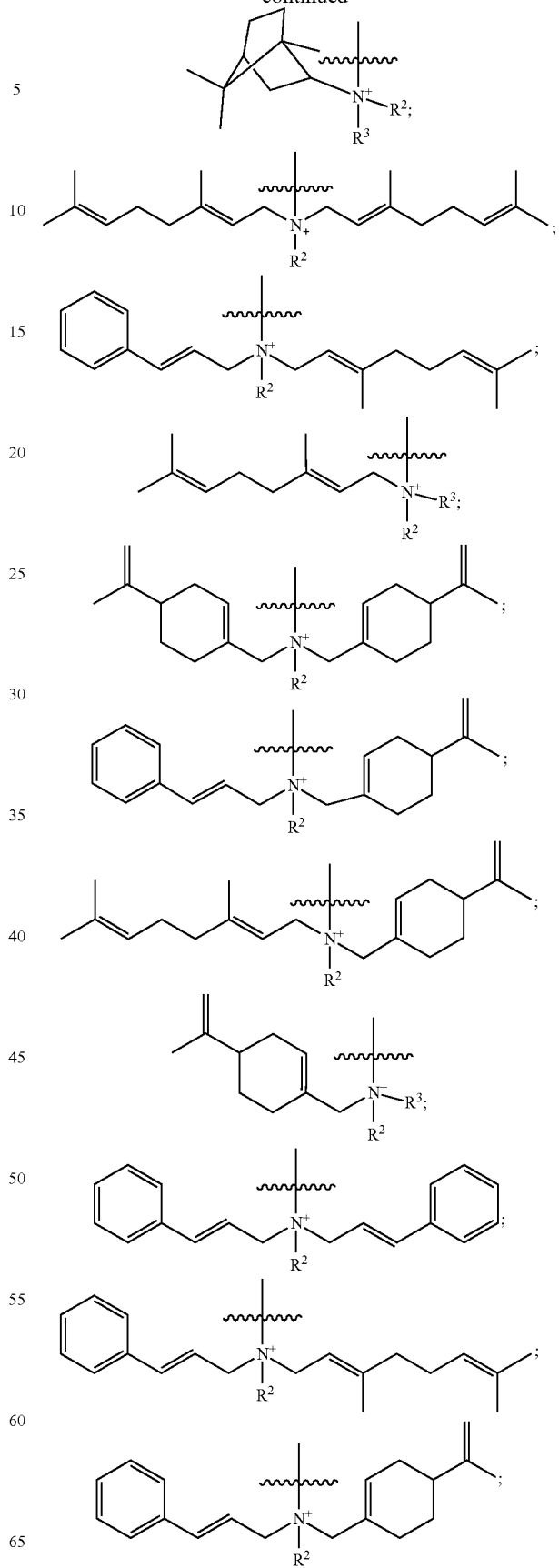

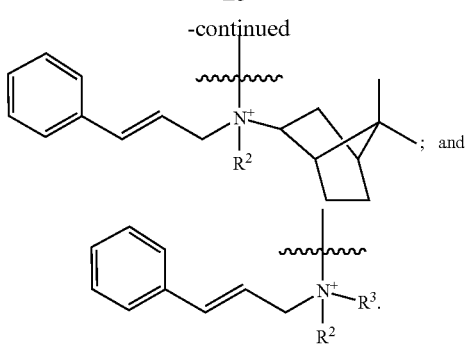

wherein $R_2$ is alkyl, terpenoid, cycloalkyl, aryl, heterocycle, a conjugated alkyl, alkenyl, alkynyl or any combination thereof;

$R_3$ is alkyl, terpenoid moiety, cycloalkyl, aryl, heterocycle, a conjugated alkyl, alkenyl, alkynyl or any combination thereof;

The particle of the present invention may be in the form of a tertiary amine, or in the form of a protonated said tertiary amine, or in the form of a quaternary ammonium salt, as described hereinabove. Since an ammonium group is positively charged, its charge should be balanced with an anion. Preferably, in a particle according to the invention this anion is a halide, e.g. fluoride, chloride, bromide or iodide, and fluoride is most preferred. Other possible anions include, but are not limited to, bicarbonate, nitrate, phosphate, acetate, fumarate, succinate and sulfate. Each possibility represents a separate embodiment of the present invention.

Anti-Microbially Active Groups Comprising One Long Alkyl Group.

In accordance with another embodiment, the anti-microbially active group of the present invention [N($R_1$)($R_2$)($R_3$)] (defined in structure 1) is a quaternary ammonium group, a tertiary amine or a tertiary ammonium, the nitrogen atom of each amine/ammonium group having at least one bond to the core (directly (i.e. in structures 1-3: X is a bond; $L_1$ in is a bond; and X' is nothing) or via a linker), at least one bond to an alkyl group having from 4 to 24 carbon atoms ($R_1$), and a remainder of bonds each being an alkyl group having 1 to 3 carbon atoms ($R_2$ and $R_3$). In another embodiment, the nitrogen atom of each amine/ammonium group having one bond to the core, one bond to an alkyl group having from 4 to 24 carbon atoms ($R_1$), and a remainder of bonds each being an alkyl group having 1 to 3 carbon atoms ($R_2$) and hydrogen or nothing ($R_3$).

Since an ammonium group is positively charged, its charge should be balanced with an anion. Any of the counter-ions described above may be used to counter-balance the quaternary ammonium group.

In some embodiments, the nitrogen atom of each quaternary ammonium or tertiary ammonium group has (i) at least one bond to the inorganic core; and (ii) at least one bond to the alkyl group having from 4 to 24 carbon atoms.

In some embodiments, the nitrogen atom of each quaternary ammonium or tertiary ammonium group has (i) at least one bond to the inorganic core; (ii) one bond to the alkyl group having from 4 to 24 carbon atoms ($R_1$), and (iii) the remainder of the bonds each being an alkyl group having from 1 to 3 carbon atoms ($R_2$ and $R_3$); or one bond is hydrogen or nothing ($R_3$) and the other bond is an alkyl group having from 1 to 3 carbon atoms ($R_2$)

The term "quaternary ammonium group" refers to a group of atoms consisting of a nitrogen atom with four substituents (different than hydrogen) attached thereto. In another embodiment, a "quaternary ammonium group" refers to a group of atoms consisting of a nitrogen atom with four groups wherein each of the group is attached to the nitrogen through a carbon atom. The term "long alkyl group" or chain refers to such an alkyl group or chain which is substituted on the nitrogen atom of the quaternary ammonium group and which has between 4 and 24 carbon atoms. In some currently preferred embodiments, the alkyl group is an alkyl group having 4 to 18 carbon atoms. In some currently preferred embodiments, the alkyl group is an alkyl group having 4 to 8 carbon atoms. In some currently preferred embodiments, the alkyl group is an alkyl group having 4 to 10 carbon atoms. In other currently preferred embodiments, the alkyl group is an alkyl group having 6, 7, or 8 carbon atoms, with each possibility representing a separate embodiment of the present invention.

In other currently preferred embodiments, the alkyl group having from 1 to 3 carbon atoms is a methyl group.

Organic Polymers Cores

In some embodiments, the core of the particles is an organic polymeric core. In one embodiment, the organic core comprises at least one aliphatic polymer. An "aliphatic polymer" as used within the scope of the present invention refers to a polymer made of aliphatic monomers that may be substituted with various side groups, including (but not restricted to) aromatic side groups. Aliphatic polymers that may be included in particles according to the present invention comprise nitrogen atoms (as well as other heteroatoms) as part of the polymeric backbone. In one embodiment, the core of the particles is an organic polymeric core including an amine which can be substituted with $R_1$, $R_2$ and/or $R_3$ as defined for the structure of formula 1; or including an imine which is chemically modified to amine and then substituted with $R_1$, $R_2$ and/or $R_3$ as defined for the structure of formula 1. Non-limiting examples of aliphatic polymers are polyethylene imine (PEI), polyvinyl amine (PVA), poly(allyl amine) (PAA), poly(aminoethyl acrylate), polypeptides with pending alkyl-amino groups, and chitosan. Each possibility represents a separate embodiment of the present invention. In one currently preferred embodiment, the polymer is polyethylene imine (PEI).

In another embodiment, the organic core comprises at least one aromatic polymer selected from the following group: aminomethylated styrene polymers, aromatic polyesters, preferably polyethylene terephthalate, and polyvinyl pyridine.

The polymeric core may be linked to the anti-microbially active group directly (i.e. in formulas 1-3: X is a bond; $L_1$ is a bond; and X' is nothing) or through a linker. Each possibility represents a separate embodiment of the present invention.

In one embodiment, the organic polymeric core includes a combination of two or more different organic polymers. In another embodiment, the organic polymeric core includes a copolymer.

In some embodiments, the anti microbial active group is linked to the organic polymeric core through a linker ($L_1$). In these embodiments, the linker may be selected from:
(a) a C1 to C18 alkylene substituted with at least one carboxyl moiety. This linker may be derived from an alkylene substituted with at least one carboxyl moiety and at least one amino moiety, wherein the carboxyl end is attached to the core and the amino end is modified to antibacterial active group [N($R_1$)($R_2$)($R_3$)]

(defined in formula 1). This linker may be derived from an amino acid of natural or synthetic source having a chain length of between 2 and 18 carbon atoms, or an acyl halide of said amino acid. Non-limiting examples for such amino acids are 18-amino octadecanoic acid and 18-amino stearic acid;

(b) a C1 to C18 alkylene. This linker may be derived from a di-halo alkylene, which is functionalized at each end with the core and anti-microbially active group, respectively, by replacement of the halogen moiety to a functional group that will bind to the core and replacement of the halogen moiety to obtain $[N(R_1)(R_2)(R_3)]$ (defined in formula 1); and (c) aromatic molecules derived from 4,4-biphenol, dibenzoic acid, dibenzoic halides, dibenzoic sulphonates, terephthalic acid, terephthalic halides, and terephthalic sulphonates. This linker is functionalized with the core and anti-microbially active group, respectively, through the functional group thereof (i.e., hydroxyl, carboxy or sulfonate). In another embodiment, this linker is attached to the core at one end and is modified at the other end to anti-microbially active group $N(R_1)(R_2)(R_3)$.

In another embodiment, the linker comprises alkyl, alkenyl, alkyl phosphate, alkyl siloxanes, carboxylate, epoxy, acylhalides and anhydrides, or combination thereof, wherein the functional group is attached to the core. Each possibility represents a separate embodiment of the present invention.

Various polymeric chains may provide a range of properties that themselves may be an accumulation of the various polymer properties, and may even provide unexpected synergistic properties. Examples of such mixed polyamine nanoparticles include: crosslinking of aliphatic and aromatic polyamines such as polyethyleneimine and poly(4-vinyl pyridine) via a dihaloalkane; mixture of linear short chain and branched high molecular weight polyethyleneimines; interpenetrating compositions of polyamine within a polyamine scaffold such as polyethyleneimine embedded within crosslinked polyvinyl pyridine nanoparticles, or even interpenetrating a polyamine into a low density non-amine scaffold such as polystyrene nanoparticles. In other words, the use of polyamine combinations for the purpose of forming nanoparticles, either by chemical crosslinking or physical crosslinking (interpenetrating networks) may afford structures of varying properties (such as being able to better kill one bacteria vs. another type of bacteria). Such properties may be additive or synergistic in nature.

In one specific embodiment, the organic polymeric core is cross-linked with a cross-linking agent. The preferred degree of cross-linking is from 1% to 20%, when crosslinking of from about 2% to about 5% is preferable. The crosslinking may prevent unfolding of the polymer and separation of the various polymeric chains that form the particle.

Crosslinking, as may be known to a person skilled in the art of organic synthesis and polymer science, may be affected by various agents and reactions that are per se known in the art. For example, crosslinking may be affected by alkylating the polymer chains with dihaloalkane such as dibromoethane, dibromocyclohexane, or bis-bromomethylbenzene. Alternatively, crosslinking by reductive amination may be used. In this method a polyamine with primary amines is reacted with a diketone or with an alkane dialdehyde to form an imine crosslinker which is then farther hydrogenated to the corresponding amine. This amine may be further reacted to form an antimicrobial effective quaternary ammonium group. In such a method, instead of dihaloalkanes or dialdehydes one may use a tri or polyhaloalkanes or polyaldehydes or polyketones.

The preferred polymers useful for making particles according to the invention are those having chains made of 30 monomer units, preferably 100 monomer units that may be crosslinked using less than 10% of crosslinking agent. The longer the polymers are, the fewer crosslinking bonds are needed to afford an insoluble nanoparticle. Branched polymers are preferred for crosslinking as small amount of crosslinking is required to form insoluble nanoparticles.

In some embodiments, at least about 10% of the amine groups in the organic polymeric core are the anti-microbially active tertiary amine/ammonium or quaternary ammonium groups or salts thereof, as described herein.

In a preferred embodiment, the particles according to the invention have functional groups that are capable of reacting with a host polymer or with monomers thereof. Such functional groups are designed to allow the particles to be bound chemically to a hosting matrix.

Inorganic Cores

In some embodiments, the core of the particles of the present invention is an inorganic core comprising one or more inorganic materials. Inorganic cores have a few advantages over organic polymeric cores: 1) higher stability at elevated temperature; 2) higher chemical stability towards various solvent and reagents; 3) improved mechanical strength; 4) better handling qualities in matrices due to their amphipathic nature; and 5) lower cost.

An additional advantage of inorganic cores relates to the insertion of the functionalized particles into a polymeric matrix. In the case where matrix polymerization involves radical polymerization (e.g. acrylate resins), inorganic cores do not interfere with the polymerization process and hence do not jeopardize the mechanical properties of the finalized substrate, as opposed to organic polymeric cores which tend to interfere with the polymerization reaction.

In one embodiment, the inorganic core comprises silica, metal, metal oxide or a zeolite. Each possibility represents a separate embodiment of the present invention.

In one embodiment, the core of the particles of the present invention comprises silica $(SiO_2)$. The silica may be in any form known in the art, non-limiting examples of which include amorphous silica, dense silica, aerogel silica, porous silica, mesoporous silica and fumed silica.

The surface density of active groups onto particle surface have proportional impact on its antibacterial activity. This is applicable both to organic and inorganic particles in same manner. In another embodiment, the core of the particles of the present invention comprises glasses or ceramics of silicate $(SiO_4^{-4})$. Non-limiting examples of silicates include aluminosilicate, borosilicate, barium silicate, barium borosilicate and strontium borosilicate.

In another embodiment, the core of the particles of the present invention comprises surface activated metals selected from the group of: silver, gold, platinum, palladium, copper, zinc and iron.

In another embodiment, the core of the particles of the present invention comprises metal oxides selected from the group of: zirconium dioxide, titanium dioxide, vanadium dioxide, zinc oxide, copper oxide and magnetite.

The inorganic core typically has a solid uniform morphology with low porosity or a porous morphology having pore size diameter of between about 1 to about 30 nm.

In another embodiment, the core of the particles of the present invention comprises natural or artificial Zeolites.

In one embodiment, the core may be attached to the anti-microbially active group directly (i.e. in formulas 1-3:

X is a bond; $L_1$ is a bond; and X' is nothing) or through a linker. Preferably a silica ($SiO_2$) based inorganic core may be attached to the anti-microbially active group through a linker, while silicates ($SiO_4^{-4}$), metals or metal oxides may be attached to the anti-microbially active group directly (i.e. in formulas 1-3: X is a bond; $L_1$ is a bond; and X' is nothing) or through a linker.

In some embodiments, the inorganic core is directly (i.e. in formulas 1-3: X is a bond; $L_1$ is a bond; and X' is nothing) attached to the anti-microbially active group. In other embodiments, the inorganic core is attached to the anti-microbially active group through a linker. In some embodiments, the linker is selected from the following groups: a C1 to C18 alkylene; a C1 to C18 alkylene substituted with at least one silane moiety; a C1 to C18 alkylene substituted with at least one phosphate moiety; a C1 to C18 alkylene substituted with at least one anhydride moiety; a C1 to C18 alkylene substituted with at least one carboxylate moiety; and a C1 to C18 alkylene substituted with at least one glycidyl moiety. Each possibility represents a separate embodiment of the present invention.

In another embodiment, the linker is represented by the structure of formula IA:

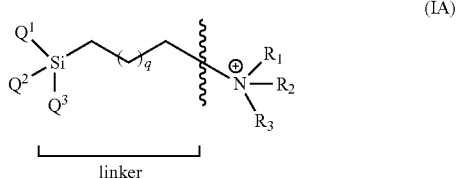

(IA)

wherein $Q^1$, $Q^2$ and $Q^3$ are independently selected from the group consisting of methoxy, ethoxy, methyl, ethyl, hydrogen, sulfonate and halide, wherein at least one of $Q^1$, $Q^2$ and $Q^3$ is selected from ethoxy, methoxy, sulfonate (e.g., mesyl, tosyl) and halide;

q is an integer between 1 and 16;

$R_1$ and $R_2$ are independently linear or branched alkyl, terpenoid, cycloalkyl, aryl, heterocycle, a conjugated alkyl, alkenyl, alkynyl or any combination thereof; and $R_3$ is nothing, hydrogen, linear or branched alkyl, terpenoid, cycloalkyl, aryl, heterocycle, a conjugated alkyl, alkenyl, alkynyl or any combination thereof;

wherein said linker is chemically bound to the core surface of the inorganic core through the silicon side.

The inorganic core of the particle as described above may generally be in a form selected from a sphere, amorphous polygonal, shallow flake-like and a rod. In some representative embodiments, the inorganic core is spherical and has a diameter between about 5 to about 100,000 nm. In some representative embodiments, the inorganic core is spherical and has a diameter between about 1000-100,000 nm. In some representative embodiments, the inorganic core is spherical and has a diameter between about 100-1000 nm with pore diameter of about 1 to about 100 nm. In another embodiment, the inorganic spherical core has a pore diameter of about 1 to about 50 nm. In another embodiment, the inorganic spherical core has a pore diameter of about 1 to about 30 nm. In another embodiment, the inorganic particle is in a form of a rod, having a diameter of between about 5 to about 1,000 nm and length between about 10 to about 1,000,000 nm. In another embodiment, a length of between 50 to 100,000 nm. In another embodiment, a length of between 100 to 250,000 nm. In another embodiment, a length of between 200 to 500,000 and a pore diameter of about 1 to about 50 nm. Each possibility represents a separate embodiment of the present invention.

Nanoparticles Embedded in a Hosting Matrix

According to another aspect, the present invention provides a composition having a liquid or solid matrix embedding a plurality of particles as described above, wherein the particles are embedded in the matrix through covalent or non-covalent interactions.

The matrix is preferably a polymeric matrix comprising a thermoplastic polymer selected from the group consisting of polyethylene, polypropylene, silicone, epoxy resin, composite materials and acrylic polymers such as poly methyl methacrylate.

Other types of substances that may serve as hosts are ceramics, composite materials of polymeric material and inorganic solids, plant powders and particles compressed into a solid article, and organic and inorganic glues. Other substances may be selected from metal coatings and other solid, semisolid or gel-like materials.

Another polymer matrix to be used in the context of the present invention is resins used in dental and orthopedic composite materials. In such applications, antibacterial particles could be first dispersed within the resin part or added simultaneously with filler or any other solid ingredients (if any). Most of these resins are acrylic or epoxy type monomers that undergo polymerization in-vivo.

In some embodiments, embedding functionalized particles into polymeric matrices may be achieved by a variety of methodologies. For example, embedding functionalized microparticles into a polypropylene host matrix was obtained by two methodologies: A) Extrusion technology: the particles were added into molten polymer, preferably into twin-coned extruder. B) Polypropylene was heated in xylene, toluene or their derivatives under reflux conditions to achieve the complete dissolution of the polymer. The antibacterial particles were then dispersed in the same solvent as used for the polymer and the mixture was added to the dissolved polymer using overhead stirrer or homogenizer. After complete dispersion of particles within the polymer, the solvent was evaporated using conventional distillation or evaporation method.

Thus, according to some embodiments, the present invention provides a method for preparing a composition comprising embedding a plurality of particles as described above, wherein the particles are embedded in the matrix, the method comprising step of adding the particles as described above, into a molten polymer matrix utilizing extrusion.

The embedment of anti-bacterial particles is mainly due to mechanical forces. These particles are "locked" between the polymer chains in a three-dimensional matrix, preventing them from migrating out from the complex network. The strong hydrophobic nature of these particles also plays a role in preventing the particles from moving into the hydrophilic surrounds such as in the case of dental, orthopedic or other medical and dental applications.

In some embodiments, particles according to the invention are homogeneously distributed on the outer surface of the matrix in a surface concentration of between about 0.1 to about 100 particles per sq. micrometer. In another embodiment, particles according to the invention are homogeneously distributed on the outer surface of the matrix in a surface concentration of between about 1 to about 100 particles per sq. micrometer The term "homogeneous distribution" is used to denote a distribution, characterized in that the standard deviation of the number of particles per sq. um is no more than the average number of particles per sq. micrometer. A homogeneous distribution is preferred for reproducibility and product specifications. If the distribution is not even, the product may exhibit different properties at different areas. The distribution of the particles away from the outer surface, that is, their bulk concentration, may be similar to that on the outer surface. As a general rule, the total surface of the particles preferably occupies at most about 20% of the surface of the matrix, preferably between 1% to 15%, more preferably between 1% and 5% and most about between 1% and 3% of the surface of the matrix.

According to some embodiments, on the average, every sq. micrometer of the outer surface of matrix has at least one particle of this invention.

The polymeric particles may be physically entrapped within the matrix, chemically bound thereto, or both. In case the particles are to be chemically bound to the host, the particles have functional groups that are capable of reacting with the host matrix (e.g., host polymer, or with monomers thereof. Thus, in some embodiments, the particles of the present invention have functional groups that are capable of reacting with a host polymer or matrix. Such functional groups are designed to allow the particles to be chemically bound to the hosting matrix.

Polymeric particles of the present invention may also include tertiary amines, tertiary ammonium or quaternary ammonium groups that are not anti-microbially active. However, the more anti-microbially active groups there are, the more preferred is the polymer, and a particle including an organic core according to the invention is characterized by having at least one anti-microbially active group per 10 sq. nm.

In one embodiment, the invention is directed to a packaging composition/material comprising a thermoplastic polymer embedded with particles of this invention. In another embodiment, the thermoplastic polymer is embedded with a mixture of two or more different particles of this invention. In another embodiment, the packaging composition/material is used in the packaging of food, beverage, pharmaceutical ingredients, medical devices, surgical equipment before operation, pre operation equipment, cosmetics, sterilized equipment/materials.

In one embodiment the packaging composition comprises a thermoplastic polymer embedded with the particles of this invention. In another embodiment, the thermoplastic polymer is polyethylene, polypropylene, silicone, epoxy resin or acrylic polymers. In another embodiment, the thermoplastic polymer is poly methylmethacrylate.

In another embodiment, the packaging composition further comprises binders, coatings, lubricants and disintegrants. In another embodiment, non limiting examples of binders include saccharides, gelatin, polyvinylpyrolidone (PVP) and polyethylene glycol (PEG). In another embodiment, non limiting examples of coatings include hydroxypropylmethylcellulose, polysaccharides and gelatin. In another embodiment, non limiting examples of lubricants include talc, stearin, silica and magnesium stearate. In another embodiment, non limiting examples of disintegrants include crosslinked polyvinylpyrolidone, crosslinked sodium carboxymethyl cellulose (croscarmellose sodium) and modified starch sodium starch glycolate.

In one embodiment, the packaging composition/material is used for packaging pharmaceutical ingredients. In another embodiment, non limiting examples of pharmaceutical ingredients include Analgesics, Antibiotics, Anticoagulants, Antidepressants, Anticancers, Antiepileptics, Antipsychotics, Antivirals, Sedatives and Antidiabetics. In another embodiment, non limiting examples of Analgesics include paracetamol, non steroidal anti inflammatory drugs (NSAIDs), morphine and oxycodone. In another embodiment, non limiting examples of Antibiotics include penicillin, cephalosporin, ciprofloxacin and erythromycin. In another embodiment, non limiting examples of Anticoagulants include warfarin, dabigatran, apixaban and rivaroxaban. In another embodiment, non limiting examples of Antidepressants include sertraline, fluoxetine, citalopram and paroxetine. In another embodiment, non limiting examples of Anticancers include Capecitabine, Mitomycin, Etoposide and Pembrolizumab. In another embodiment, non limiting examples of Antiepileptics include Acetazolamide, Clobazam, Ethosuximide and lacosamide. In another embodiment, non limiting examples of Antipsychotics include Risperidone, Ziprasidone, Paliperidone and Lurasidone. In another embodiment, non limiting examples of Antivirals include amantadine, rimantadine, oseltamivir and zanamivir. In another embodiment, non limiting examples of Sedatives include Alprazolam, Clorazepate, Diazepam and Estazolam. In another embodiment, non limiting examples of Antidiabetics include glimepiride, gliclazide, glyburide and glipizide.

In one embodiment, the packaging composition/material is used in the packaging of food ingredients. In another embodiment, non limiting examples of food ingredients packaged with the packaging material of the invention include preservatives, sweeteners, color additives, flavors and spices, nutrients, emulsifiers, binders and thickeners. In another embodiment, non limiting examples of preservatives include Ascorbic acid, citric acid, sodium benzoate, calcium propionate, sodium erythorbate and sodium nitrite. In another embodiment, non limiting examples of sweeteners include Sucrose (sugar), glucose, fructose, sorbitol, mannitol and corn syrup. In another embodiment, non limiting examples of color additives include Orange B, Citrus Red No. 2, annatto extract, beta-carotene, grape skin extract, cochineal extract or carmine and paprika oleoresin. In another embodiment, non limiting examples of flavors and spices include monosodium glutamate, glycine slats, inosinic acid, isoamyl acetate, limonene and allyl hexanoate. In another embodiment, non limiting examples of nutrients include Thiamine hydrochloride, riboflavin (Vitamin $B_2$), niacin, niacinamide, folate or folic acid. In another embodiment, non limiting examples of emulsifiers include Soy lecithin, mono- and diglycerides, egg yolks, polysorbates and sorbitan monostearate. In another embodiment, non limiting examples of binders and thickeners include Gelatin, pectin, guar gum, carrageenan, xanthan gum and whey.

Preparation of Particles

The particles of the present invention may be prepared in accordance with a variety of processes, depending on the nature of the core, the anti-microbially active group, and the presence or absence of linkers. Some non-limiting examples of preparation methods are provided below.

The particles of this invention comprise a core and an anti-microbially active group $[N(R_1)(R_2)(R_3)]$ linked directly (i.e. in formulas 1-3: X is a bond; $L_1$ is a bond; and X' is nothing) or via a linker ($L_1$-X) as presented by the structures of formulas 1-3:

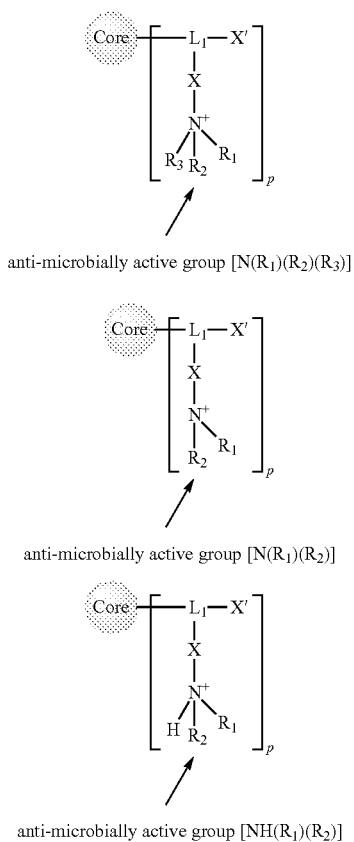

(1) anti-microbially active group [N(R$_1$)(R$_2$)(R$_3$)]

(2) anti-microbially active group [N(R$_1$)(R$_2$)]

(3) anti-microbially active group [NH(R$_1$)(R$_2$)]

wherein
the core is an organic polymeric material, an inorganic material, a metal or a meta oxide;
L$_1$ is a linker or a bond;
R$_1$ is alkyl, terpenoid, cycloalkyl, aryl, heterocycle, a conjugated alkyl, alkenyl, alkynyl or any combination thereof;
R$_2$ is alkyl, terpenoid, cycloalkyl, aryl, heterocycle, a conjugated alkyl, alkenyl, alkynyl or any combination thereof;
R$_3$ is nothing, hydrogen, alkyl, terpenoid moiety, cycloalkyl, aryl, heterocycle, a conjugated alkyl, alkenyl, alkynyl or any combination thereof;
X is a bond, alkyl, alkenyl, or alkynyl;
X' is nothing or hydrogen; and
p is the number of chains per one sq nm (nm$^2$) of the core surface, wherein the anti microbial active group is at a surface density of between 0.001-20 anti microbial active groups per one sq nm (nm$^2$) of the core surface of the particle;
wherein if L$_1$ and X are bonds, then the nitrogen is an integral part of the core;
wherein at least one of R$_1$, R$_2$, R$_3$ is hydrophobic.

Particles where the anti-microbially active group [N(R$_1$)(R$_2$)(R$_3$)] linked directly (i.e. in formulas 1-3: X is a bond; L$_1$ is a bond; and X' is nothing) to the core comprising (i) an organic polymer core; and (ii) anti-microbially active groups selected from the group consisting of (a) a tertiary amine (i.e. R$_3$ is nothing) or tertiary ammonium (i.e. R$_3$ is hydrogen) comprising at least one terpenoid moiety (b) a quaternary ammonium group comprising at least one terpenoid moiety (c) a quaternary ammonium group, comprising at least one alkyl group having from 4 to 24 carbon atoms; and (d) a tertiary amine (i.e. R$_3$ is nothing) or tertiary ammonium (i.e. R$_3$ is hydrogen) comprising at least one alkyl group having from 4 to 24 carbon atoms; may be prepared by functionalizing the polymeric core with said tertiary amine or said quaternary ammonium group as described above.

Particles where the anti-microbially active group [N(R$_1$)(R$_2$)(R$_3$)] linked directly (i.e. in formulas 1-3: X is a bond; L$_1$ is a bond; and X' is nothing) to the core comprising (i) an organic polymer core; and (ii) anti-microbially active groups selected from the group consisting of (a) a tertiary amine or tertiary ammonium (i.e. R$_3$ is nothing or H) comprising at least one terpenoid moiety and optionally an alkyl group having from 1 to 4 carbon atoms, or a salt of said amine (i.e. R$_1$ and R$_2$ are terpenoid moieties or R$_1$ is a terpenoid moiety and R$_2$ is a C$_1$-C$_4$ alkyl); (b) a quaternary ammonium group comprising at least one terpenoid moiety and optionally one or more alkyl groups having from 1 to 4 carbon atoms (i.e. R$_1$, R$_2$ and R$_3$ are terpenoid moieties; or R$_1$ and R$_2$ are terpenoid moieties and R$_3$ is C$_1$-C$_4$ alkyl or R$_1$ and are terpenoid moieties and R$_2$ is C$_1$-C$_4$ alkyl; or R$_1$ is a terpenoid moiety and R$_2$ and R$_3$ are C$_1$-C$_4$ alkyl); (c) a quaternary ammonium group, the nitrogen atom of each quaternary ammonium group having at least one bond to an alkyl group having from 4 to 24 carbon atoms, and a remainder of bonds each being to an alkyl group having from 1 to 3 carbon atoms (i.e. R$_1$, R$_2$ and R$_3$ are a C$_4$-C$_{24}$ alkyl or R$_1$ and R$_2$ are C$_4$-C$_{24}$ alkyl and R$_3$ is C$_1$-C$_3$ alkyl or R$_1$ and R$_3$ are C$_4$-C$_{24}$ alkyl and R$_2$ is C$_1$-C$_3$ alkyl; or R$_1$ is a C$_4$-C$_{18}$ alkyl and R$_2$ and R$_1$ are C$_1$-C$_3$ alkyl; and (d) a tertiary amine or tertiary ammonium (i.e. R$_3$ is nothing or H) comprising at least one bond to an alkyl group having from 4 to 24 carbon atoms, and a remainder of bonds each being an alkyl group having from 1 to 3 carbon atoms; may be prepared by functionalizing the polymeric core with said tertiary amine or said quaternary ammonium group as described above.

Particles comprising (i) an inorganic polymer core; and (ii) anti-microbially active groups selected from the group consisting of (a) a tertiary amine (i.e. R$_3$ is nothing) or tertiary ammonium (i.e. R$_3$ is hydrogen) comprising at least one terpenoid moiety (b) a quaternary ammonium group comprising at least one terpenoid moiety (c) a quaternary ammonium group, comprising at least one alkyl group having from 4 to 24 carbon atoms; and (d) a tertiary amine (i.e. R$_3$ is nothing) or tertiary ammonium (i.e. R$_3$ is hydrogen) comprising at least one alkyl group having from 4 to 24 carbon atoms; may be prepared by reacting the inorganic core with a linker moiety L$_1$ to create a surface functionalized core; and functionalizing the obtained product to generate a tertiary amine, tertiary ammonium or said quaternary ammonium group as described above. Each possibility represents a separate embodiment of the invention.

Particles comprising (i) an inorganic polymer core; and (ii) anti-microbially active groups selected from the group consisting of (a) a tertiary amine ((i.e. R$_3$ is nothing) or tertiary ammonium (R$_3$ is H) comprising at least one terpenoid moiety and optionally an alkyl group having from 1 to 4 carbon atoms, or a salt of said amine (i.e. R$_1$ and R$_2$ are terpenoid moieties or R$_1$ is a terpenoid moiety and R$_2$ is a C$_1$-C$_4$ alkyl); and (b) a quaternary ammonium group comprising at least one terpenoid moiety and optionally one or more alkyl groups having from 1 to 4 carbon atoms (i.e. R$_1$, R$_2$ and R$_3$ are terpenoid moieties; or R$_1$ and R$_1$ are terpenoid moieties and R$_3$ is C$_1$-C$_4$ alkyl or R$_1$ and R$_3$ are terpenoid moieties and R$_2$ is C$_1$-C$_4$ alkyl; or R$_1$ is a terpenoid moiety and R$_2$ and R$_3$ are C$_1$-C$_4$ alkyl), may be prepared by reacting the inorganic core with a linker moiety L$_1$ to create a surface functionalized core; and functionalizing the obtained product to generate a tertiary amine, tertiary ammonium or said quaternary ammonium group as described above.

Particles comprising (i) an inorganic core; and (ii) anti-microbially active groups comprising a quaternary ammonium group chemically bound to one alkyl group having from 4 to 24 carbon atoms and a reminder of bonds each being to an alkyl group having from 1 to 3 carbon atoms (i.e. $R_1$, $R_2$ and $R_3$ are a $C_4$-$C_{24}$ alkyl or $R_1$ and $R_2$ are $C_4$-$C_{24}$ alkyl and $R_3$ is $C_1$-$C_3$ alkyl or $R_1$ and $R_3$ are $C_4$-$C_{24}$ alkyl and $R_2$ is $C_1$-$C_3$ alkyl; or $R_1$ is a $C_4$-$C_{24}$ alkyl and $R_2$ and $R_3$ are $C_1$-$C_3$ alkyl, may be prepared by (i) reacting said inorganic core with a linker moiety $L_1$ to create a primary amine surface functionalized core; and (ii) functionalizing the product of step (a) to generate a quaternary ammonium group.

Alternatively, particle comprising (i) an inorganic core; and (ii) anti-microbially active groups comprising a quaternary ammonium group chemically bound to one alkyl group having from 4 to 24 carbon atoms and a reminder of bonds each being to an alkyl group having from 1 to 3 carbon atoms (i.e. $R_1$, $R_2$ and $R_3$ are a $C_4$-$C_{24}$ alkyl or $R_1$ and $R_2$ are $C_4$-$C_{18}$ alkyl and is $C_1$-$C_3$ alkyl or $R_1$ and $R_3$ are $C_4$-$C_{24}$ alkyl and $R_2$ is $C_1$-$C_3$ alkyl; or $R_1$ is a $C_4$-$C_{24}$ alkyl and $R_2$ and $R_3$ are $C_1$-$C_3$ alkyl), may be prepared by (i) reacting the inorganic core with a linker moiety comprising of a leaving group selected from ethoxy, methoxy, sulfonate and halide; and (ii) functionalizing the product of step (a) to generate a quaternary ammonium group as described above.

As contemplated herein, inorganic core-linker-anti-microbially active group adduct may be formed using a variety of reagents. The choice of the reagent depends on the nature of the anti-microbially active group. For example, when the anti-microbially active group is a tertiary amine/ammonium or a quaternary ammonium group comprising at least one terpenoid moiety, a preferred reagent for coupling the inorganic core to the anti-microbially active group is represented by the structure of formula (I):

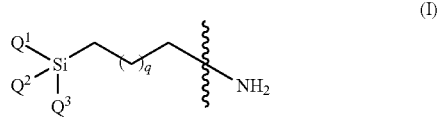

(I)

wherein
$Q^1$, $Q^2$ and $Q^3$ are independently selected from the group consisting of alkoxy, methyl, ethyl, hydrogen, sulfonate and halide, wherein at least one of $Q^1$, $Q^2$ and $Q^3$ is selected from ethoxy, methoxy, sulfonate (e.g., mesyl, tosyl) and halide; and q is an integer between 1 and 16;
wherein the reagent is capable of being chemically bound to the surface of the inorganic core through the silicon atom, and wherein the anti-microbially active group is introduced by functionalizing the primary amine to obtain an anti-microbially active tertiary amine or quaternary ammonium group containing at least one terpenoid group, as described above.

Alternatively, when the anti-microbially active group is a quaternary ammonium group containing one alkyl group having 4 to 24 carbon atoms, a preferred reagent for coupling the inorganic core to the anti-microbially active group is represented by the structure of formula (II):

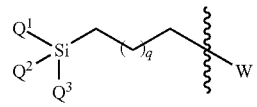

(II)

wherein
$Q^1$, $Q^2$ and $Q^3$ are independently selected from the group consisting of alkoxy, methyl, ethyl, hydrogen, sulfonate and halide, wherein at least one of $Q^1$, $Q^2$ and $Q^3$ is selected from ethoxy, methoxy, sulfonate (e.g., mesyl, tosyl) and halide;

W is selected from the group consisting of $NH_2$, halide, sulfonate and hydroxyl;
and q is an integer between 1 and 16;
wherein said linker is capable of being chemically bound to the surface of said inorganic core through the silicon atom, and wherein the anti-microbially active group is introduced by substituting the group W with an anti-microbially active group, or converting the group W to an anti-microbially active group.

It will be apparent to a person of skill in the art that other linker moieties may be used, depending on the desired linker group. A person of skill in the art will know to design reagents and reactions to prepare other linkers contemplated by the present invention, e.g., a C1 to C18 alkylene substituted with at least one phosphate moiety; a C1 to C18 alkylene substituted with at least one anhydride moiety; a C1 to C18 alkylene substituted with at least one carboxylate moiety; and a C1 to C18 alkylene substituted with at least one glycidyl moiety.

Figure 12:
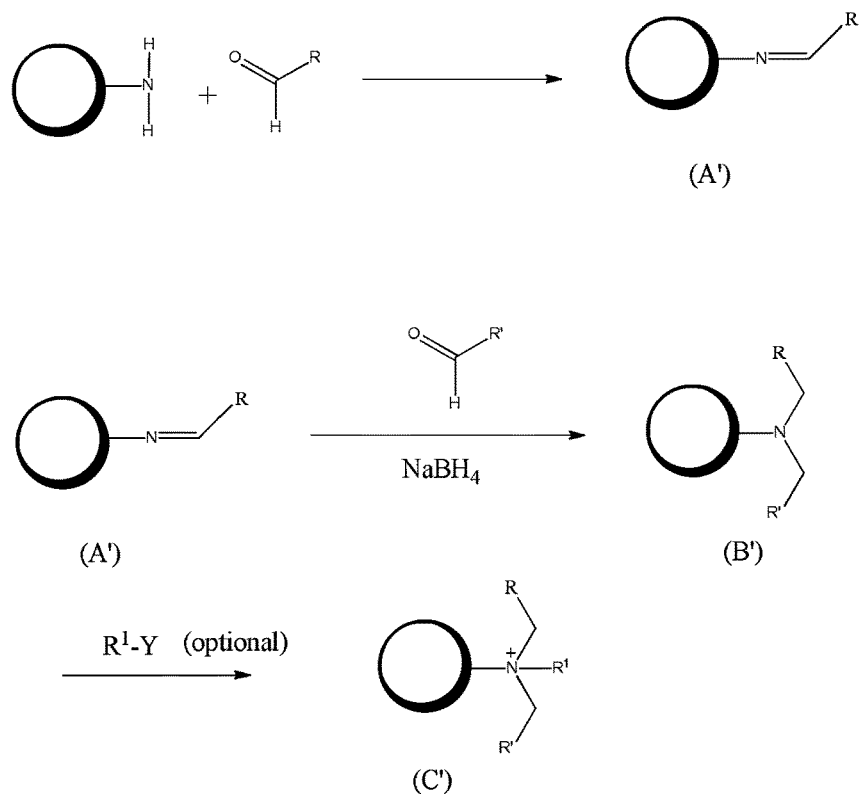
FIG. 12: A representative scheme of preparation of particles according to the present invention wherein the antimicrobially active group a tertiary amine or a quaternary ammonium group comprising at least one terpenoid moiety.

A representative method for preparing particles according to the present invention wherein the anti-microbially active group a tertiary amine or a quaternary ammonium group comprising at least one terpenoid moiety is represented in FIG. 12. In accordance with FIG. 12, a core as defined herein is functionalized with a primary amine. The primary amine reacts with an aldehyde to yield initially an imine (Schiff base) intermediate of formula (A'), which is then reacted with a second aldehyde under reductive amination conditions to yield a tertiary amine of formula (B'). RC(=O)H and R'C(=O)H each represent an aldehyde which is a terpenoid or which is derived from a terpenoid. RC(=O)H and R'C(=O)H may be the same or different from each other. Conversion of the tertiary amine to the quaternary ammonium group is optional, and involves reaction of the tertiary amine with a group $R^1$—Y wherein $R^1$ is a $C_1$-$C_4$ alkyl and Y is a leaving group such as halogen or sulfonate.

It is understood that that the group

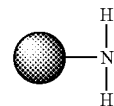

may represents any one or more of the following:
1. An organic core directly bound to $NH_2$.
2. An organic core bound to $NH_2$ through a linker as described herein.
3. An inorganic core directly bound to $NH_2$.
4. An inorganic core bound to $NH_2$ through a linker as described herein.

The exemplified reaction may be a "one pot synthesis", or it may include two sequential reactions with isolation of an intermediate formed in the first step. The first step is the formation of intermediate (A'), which is an imine (Schiff base), by reacting an amine functionalized core with a terpenoid moiety in the presence of a reducing agent, in this case cinnamyl in the presence of $NaBH_4$. The imine functionalized core can be isolated at this stage if desired. Alternatively, further reacting intermediate (A') with a terpenoid moiety in the presence of a reducing agent yields a tertiary amine comprising two terpenoid moieties (B'). In order to obtain the quaternary ammonium, additional alkylation step is performed as described in FIG. 12.

Figure 13:
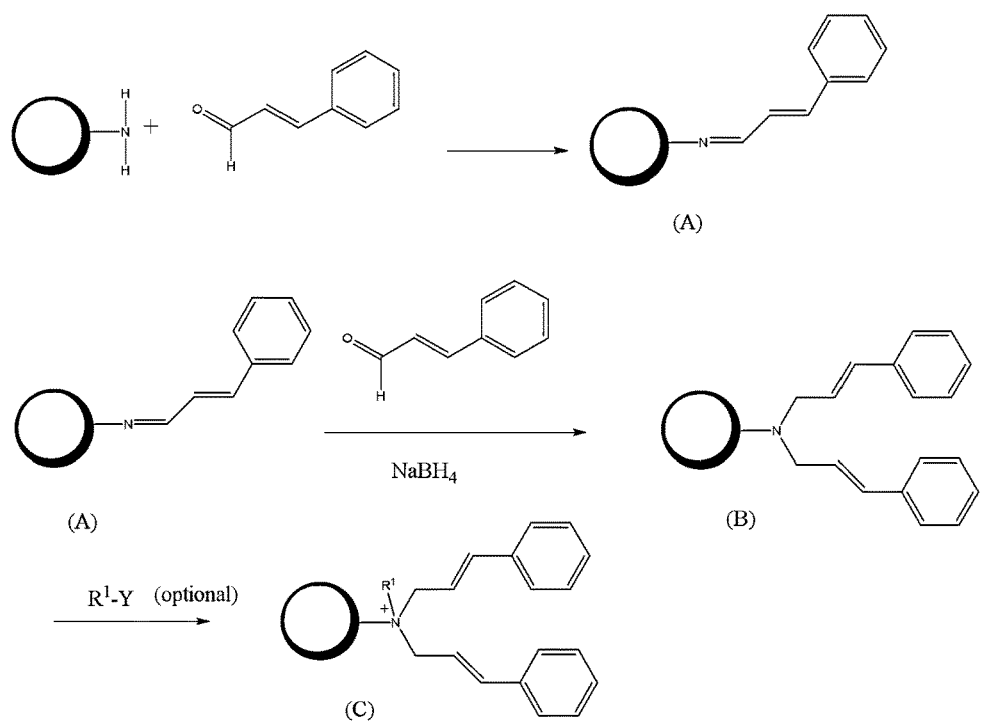
FIG. 13: A Representative scheme of preparation of cinnamyl adduct product with core particle via aminofunctional linker. Conversion of the tertiary amine to the quaternary ammonium group is optional, and involves reaction of the tertiary amine with a group $R^1$—Y wherein $R^1$ and Y are as defined above.

This process is exemplified in FIG. 13 for cinnamaldehyde, but is applicable to other aldehydes.

The imine particle which is an intermediate in the process for preparing the anti-microbially active particles, is new, and represents a separate embodiment of the present invention. Thus, in some embodiments, the present invention provides a particle comprising (i) an inorganic core or an organic polymeric core; and (ii) an imine moiety chemically bound to the core, preferably at a surface density of at least one imine group per 10 sq. nm, wherein the imine group comprises a terpenoid moiety. The imine moiety is generally represented by the structure of formula (B') in FIG. 12. A more specific embodiment is the structure of formula (B) in FIG. 13. It is understood by a person of skill in the art that other imine intermediate compounds comprising other terpenoids groups as described herein, are also encompassed by the present invention.

Figure 14A:
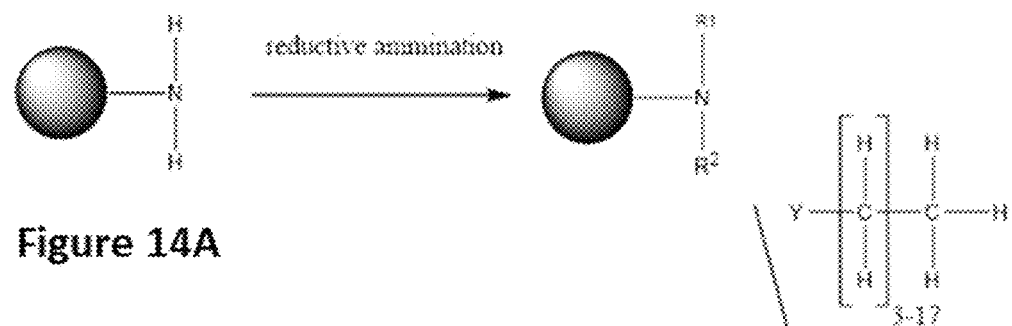
FIGS. 14A-14C: A representative scheme of three pathways to prepare quaternary ammonium salts (QAS) functionalized particle.
Figure 14B:
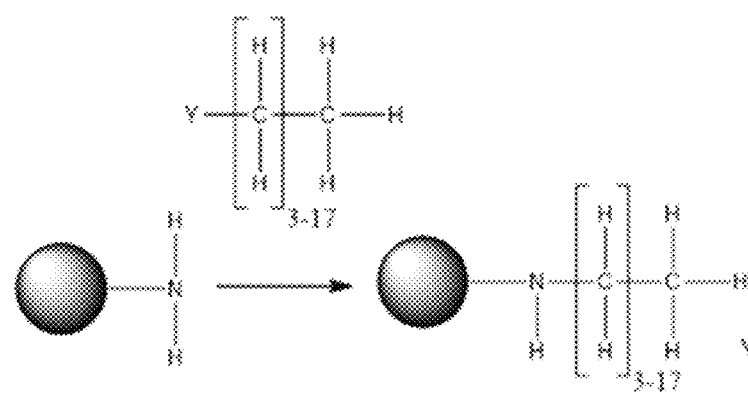
Figure 14C:
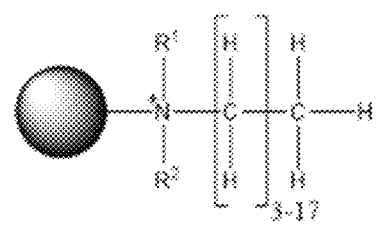
Figure 14C:
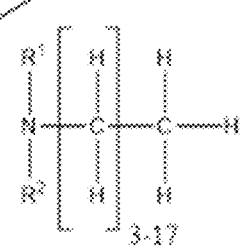

A representative method for preparing particles according to the present invention wherein the anti-microbially active group is a quaternary ammonium group containing one alkyl group having 4 to 18 carbon atoms is presented in FIGS. 14A-14C. The method includes three pathways to prepare quaternary ammonium salts (QAS) functionalized particle. FIG. 14A) by first utilizing reductive amination to achieve tertiary amine, followed by an alkylation reaction, FIG. 14B) by stepwise alkylation reactions; and FIG. 14C) by reacting a linker functionalized with a leaving group (e.g., Cl or other halogen) with tertiary amine. $R^1$ and $R^2$ represent $C_1$-$C_3$ alkyls such as methyl, ethyl, propyl or isopropyl. $R^1$ and $R^2$ may be different or the same group. Y represents any leaving group, for example Cl, Br or I, or a sulfonate (e.g., mesyl, tosyl).

It is understood that that the group

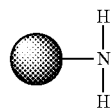

has any one of the meanings as described above for FIGS. 12 and 13.

It is understood that that the group

may represents any one or more of the following:
1. An organic core directly bound to Y.
2. An organic core bound to Y through a linker as described herein.
3. An inorganic core directly bound to Y.
4. An inorganic core bound to Y through a linker as described herein.

Preparation of Core Particles

Porous silica materials can be prepared by reaction of $SiCl_2$ with alcohol or water, followed by drying using centrifugation and/or heating utilizing airflow or under vacuum conditions. Dense fumed silica particles (pyrogenic) were prepared by pyrolysis of $SiCl_4$.

An alternative preparation method of silica core material can be carried by the hydrolysis of tetraethylorthosilicate (TEOS) or tetramethyl orthosilicate (TMS) in the presence of alcohol or water solution and under basic (Stober) or acidic catalytic conditions.

Mesoporous silica particles can be prepared by hydrolysis of TEOS or TMS at low temperatures, preferably in a temperature not exceeding 60° C., followed by dehydration by centrifugation and/or evaporation under airflow or vacuum conditions.

Dense particles can be prepared utilizing intense heating in a process called calcination. Typically, such process takes place at high temperatures at about 250° C.

Figure 15:
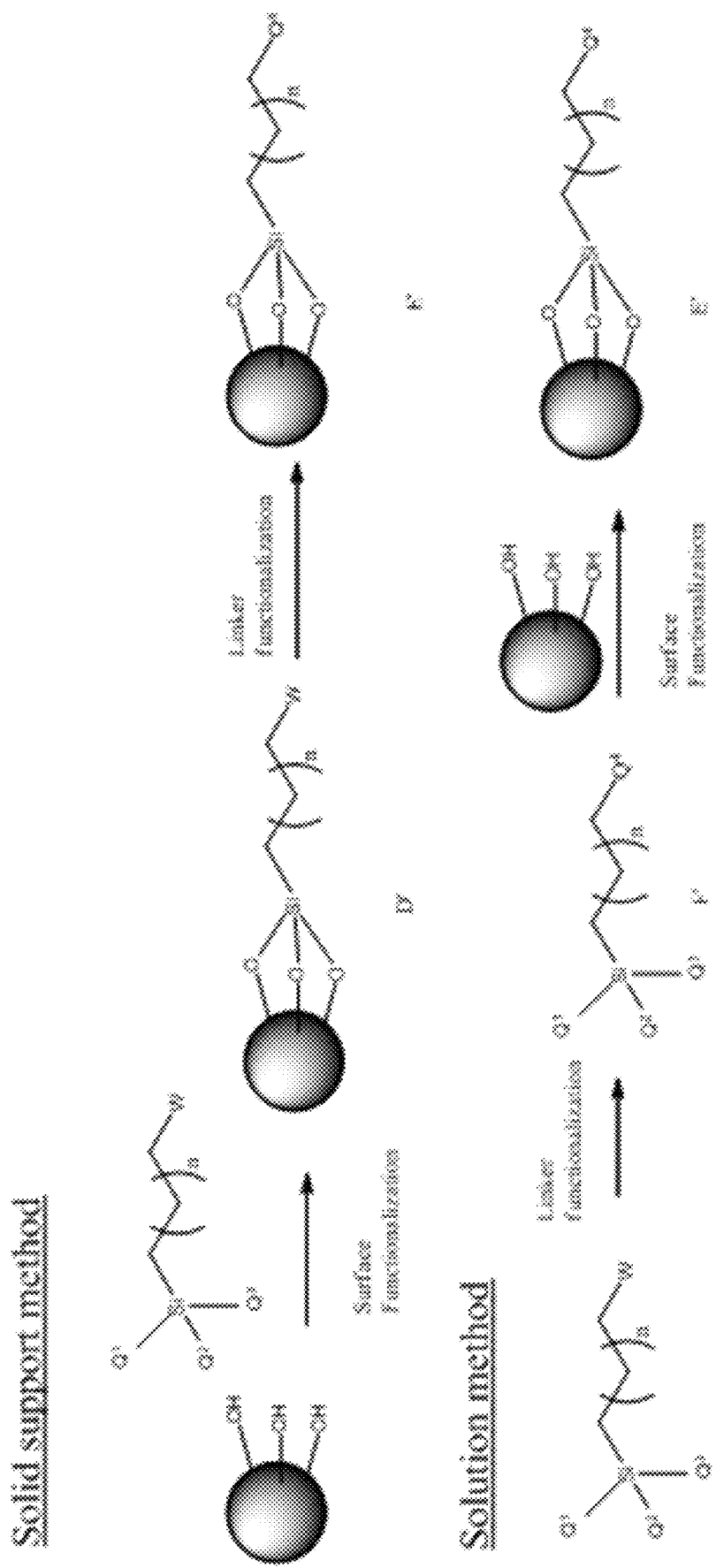
FIG. 15: Schemes of solid support and solution methods for the preparation of particles of this invention. Functionalization. $Q^1$, $Q^2$ and $Q^3$ are independently selected from the group consisting of ethoxy, methoxy, methyl, ethyl, hydrogen, sulfonate and halide, wherein at least one of $Q^1$, $Q^2$ and $Q^3$ is a leaving group selected from ethoxy, methoxy, sulfonate (e.g., mesyl, tosyl) and halide. For the sake of clarity the scheme presents a case where $Q^1$, $Q^2$, and $Q^3$ represent leaving groups; $Q^4$ represents ab anti-microbial group; W is from the group consisting of $NH_2$, halide, sulfonate and hydroxyl; and n is an integer between 1 and 16.

Core preparation and functionalization can occur by a solid support method, or a solution method (FIG. 15).

Solid Support Method

Preparation of functionalized particles is conducted in two general steps. First, the linker molecule is allowed to condense onto particles surface (surface functionalization) via hydrolysis of leaving groups to give an intermediate of formula (FIG. 15, D'). Second, functional sites of the linker molecule undergo further functionalization (linker functionalization) as mentioned in any ones of (FIGS. 12-14) to give a functionalized particle of formula (E').

Solution Method

In this method, the linker molecule is first functionalized with antimicrobial active group to give an intermediate of formula (FIG. 15, F'). In the second stage intermediate (F') is allowed to settle onto particle's solid surface (surface functionalization) to give a functionalized particle of formula (FIG. 15, E').

Figure 16:
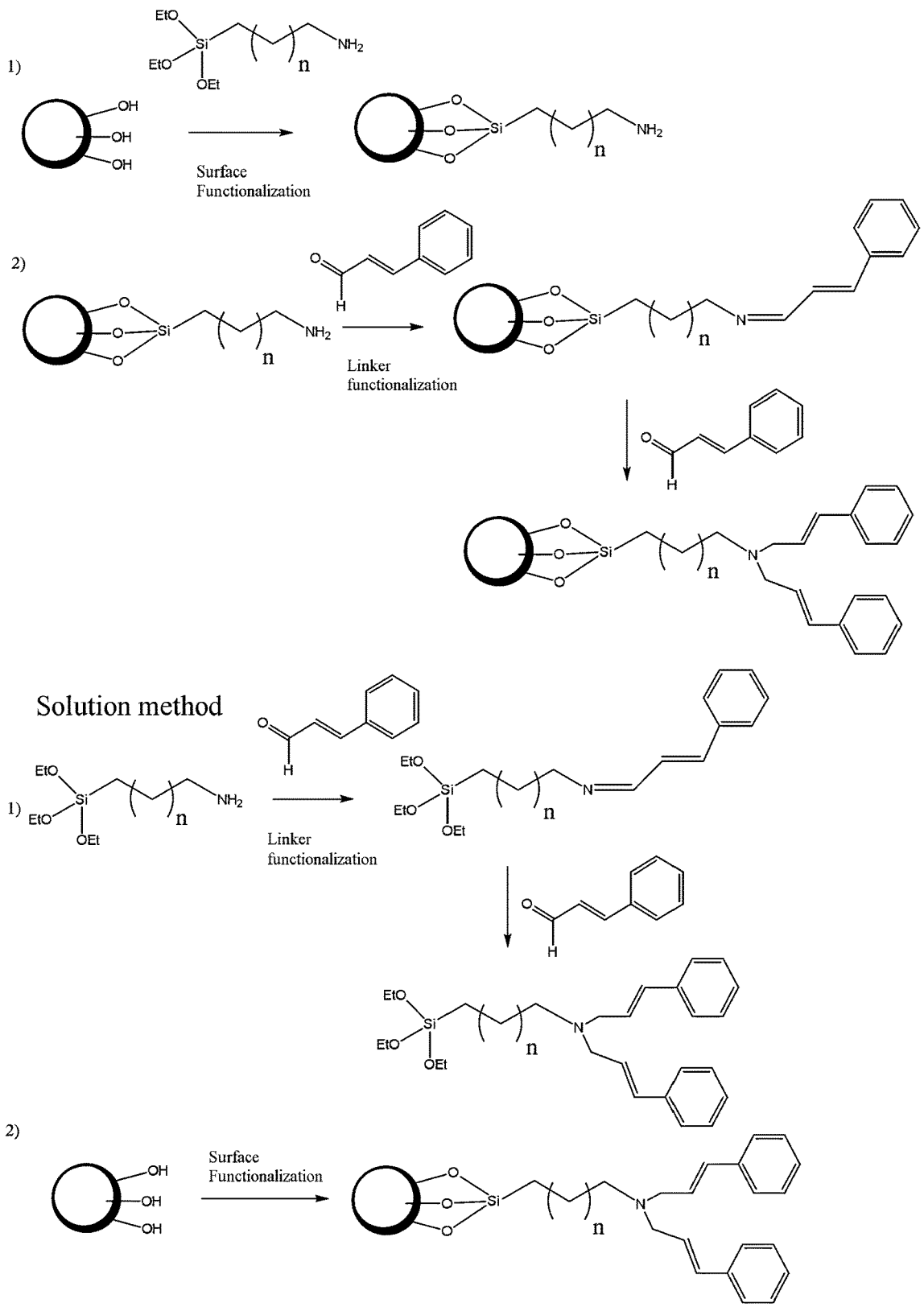
FIG. 16: A representative scheme of preparation of di-cinnamyl adduct product with core particle functionalized utilizing a 12-(triethoxysilyl)-dodecan-1-amine linker by both solid support method and solution method. n is an integer of 1 to 16.

This process is exemplified in FIG. 16 for cinnamaldehyde, but is applicable to other aldehydes.

Methods of Inhibition of Bacteria

According to another aspect of the invention there is provided a method for inhibition of bacteria, by contacting the bacteria with the nanoparticle or microparticle of the present invention, or a composition comprising the particles of this invention. The term "inhibition" is used to denote destruction, i.e. annihilation, of at least 99% of the bacteria, preferably 99.9%, most preferably 99.99% of the bacteria; reduction in the growth rate of the bacteria; reduction in the size of the population of the bacteria; prevention of growth of the bacteria; causing irreparable damage to the bacteria; destruction of a biofilm of such bacteria; inducing damage, short term or long term, to a part or a whole existing biofilm; preventing formation of such biofilm; inducing biofilm management; or bringing about any other type of consequence which may affect such population or biofilm and impose thereto an immediate or long term damage (partial or complete).

The term "biofilm" refers to a population of biological species (bacteria) attached to a solid surface.

The terms "anti-microbial" and "anti-bacterial" are used herein interchangeably. The quaternary ammonium and the tertiary amine groups of this invention [N(R1)(R2)(R3)] provide the anti-microbial activity. The quaternary ammonium's activity remains strong at any pH. Tertiary amines have high pKa values, therefore are active at almost all pH levels (up to 10, but not higher). The tertiary amine functional groups are less likely to cause undesirable side effects such as irritation of soft tissue, if used in contact with skin or mucosa or if used as a pharmaceutical composition.

In a preferred embodiment, the inhibition is achieved by contacting the bacteria with a matrix containing up to 5% w/w, more preferably up to 1% particles according to the present invention, or compositions comprising them.

Accordingly, compositions according to the invention may find utility in a broad range of applications, where decontamination or growth prevention of bacteria is required, as, for example in medicine artificial replacement of tissues such as bone, bone cements and joints (orthopedic), lenses (ophthalmology), blood vessels and stents, artificial heart valves (cardiology), artificial skin, implants (plastic surgery), intra uterin devices (gynecology), neurosurgical shunts, medical devices, stents, uretral stents coating for subcutaneous implants: insulin pumps, contraceptives, pacemakers, tubing and canulas used for intra venous infusion, tubing and canulas used for dialysis, surgical drainage tubing, urinary catheters, endotracheal tubes, wound covering materials, sutures, catheters of all kinds that are inserted temporarily or permanently in blood vessels as well as the urinary system, shunt for use in brain applications, surgical gloves, tips for ear examination, statoscope ends and other elements used by the medical personnel; tooth pastes, tooth brushes, tooth pick, dental floss, and interdental and tongue brushes, ointments and creams used for dermatology or in the cosmetic industry, plastic wear for medical and research laboratories; food packaging, mainly for dairy products and fresh meat and fish; paints for ships, that prevent growth of biofilm, paints for bathrooms, paint for hospitals and clean rooms and many others. In some embodiments, the particles or composition comprising thereof are used for dental and orthopedic resin based cements, sealers, composite materials, adhesives and cements; for dental and orthopedic metal implants and wires; for surgical sutures; for catheters, metal surgical tools, non-surgical medical devices.

One preferred use of the compositions of the present invention is in dentistry: dental adhesives, dental restorative materials such as all types of composite based materials for filling tooth-decay cavities, endodontic filling materials (cements and fillers) for filling the root canal space in root canal treatment, materials used for provisional and final tooth restorations or tooth replacement, including but not restricted to inlays, onlays, crowns, partial dentures (fixed or removable) dental implants, and permanent and temporary cements used in dentistry for various known purposes.

In one particular embodiment, the particle or composition of the present invention is intended for administration into an oral cavity. The composition may be formulated as a tooth paste, and/or may be applied to a surface or medical device selected from the group consisting of: a denture cleaner, post hygienic treatment dressing or gel, mucosal adhesive paste, a dental adhesive, a dental restorative composite based material for filling tooth, decay cavities, a dental restorative endodontic filling material for filling root canal space in root canal treatment, a dental restorative material used for provisional and final tooth restorations or tooth replacement, a dental inlay, a dental onlay, a crown, a partial denture, a complete denture, a dental implant and a dental implant abutment.

The antimicrobial property may protect the patient and the medical staff from cross contamination from patient to patient or from patient to the examiner. Self-sterilizing packaging for medicines and items that enter the operation room are also beneficial. Applications out of the medical field may for example be in athlete shoes or the inner part of a shoe wherein bacteria tend to collect, tooth brushes and any brush that comes in contact with the human body, pet cages as well as other veterinary items, etc.

In one embodiment, the invention directs to any particle disclosed above. In another embodiment, the invention is directed to a composition of mixture comprising any particle disclosed above.

The following non-limiting examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Preparation of Core Particles of Amorphous $SiO_2$ (Silica)

Silica dioxide core particles were prepared by hydrolysis of tetraalcoxy silicate under alkaline conditions. The reaction solution was prepared by mixing 9 parts by weight of ethanol, 0.4 parts of deionized water and 0.1 part of ammonia, keeping the pH within the range of 10-14. Controlling the particle size and the reaction rate is achieved by adjusting the concentration of water and ammonia in the reaction solution. 0.5 parts of tetraethyl orthosilicate (TEOS) was added to the solution in one portion with stirring at 1,000 RPM for 1 hour. The reaction mixture first turned opaque, followed by a white solid precipitation, indicating the reaction endpoint and agglomerates formation of primary particles. The particles were recovered by centrifugation filtration, rinsing with 20 parts of deionized water and drying using freeze drying or heating. Optionally, further surface activation may be performed by shortly rinsing particles in sulfuric acid/hydrogen peroxide solution commonly known as "pirhana solution". This last step converts most of the particles' surface into hydroxyl form and promotes an efficient surface functionalization.

Example 2: Morphological Characterization of Silica Particles

Nitrogen adsorption method was used to determine the morphology of porous silica dioxide particles by utilizing Barrett-Joyner_Halenda (BJH) model. Non-functionalized mesoporous silica dioxide particles were rinsed in Milli-Q water, dried and then degassed. Pore size was obtained from the adsorption/desorption isotherm by applying BJH model. Average particle size measured using dynamic light scattering method. Therefore, said particles are of 186 nm in diameter and having pore size of 5.0 nm.

Example 3: Preparation of Magnetite Core Particles

Magnetite ($Fe_3O_4$) particles were prepared by co-precipitation of $Fe^{2+}$ and $Fe^{3+}$ ions, from $FeCl_2$ (1 mol eq) and $FeCl_3$ (0.5 mol eq) in aqueous solution in basic condition utilizing $NH_4OH$ (pH~12). After precipitation, the particles recovered under constant magnetic field. Prior to functionalization, particles were rinsed in water followed by vacuum drying. Surface activation of the obtained magnetite particles was performed by a short rinse of the particles in nitric acid or sulfuric acid and hydrogen peroxide solution. The last step converted most of particles' surface into hydroxy form allowing further functionalization of the core.

Example 4: Surface Functionalization of Inorganic Core Particles

Functionalization of silica particles was performed in two stages. Initially, primary amine-functionalized silica particles were prepared. The primary amine was the functionalized by reductive amination to yield a tertiary amine comprising terpenoid groups, or alternatively a quaternary ammonium group comprising one elongated alkyl chain of 8 carbons.

(a) Preparation of Primary Amine-Functionalized Silica Particles

Dry silica particles were dispersed in 1:9 water/ethanol solution, and the pH of the mixture was adjusted to ~4.5 by the addition of glacial acetic acid. 3-aminopropyl triethoxy silane (APTS) was added to the reaction mixture in an amount that does not exceed 4% wt/v of the total reaction mixture. The reaction was conducted at a temperature of 60° to 80° C. for about 1-3 hours. Subsequently, the amine-functionalized particles were recovered by rinsing/drying method utilizing purified water, then rinsed in alkaline solution of $NaHCO_3$, and were left to dry.

A pretreatment of inorganic cores (for example $SiO_2$, $Fe_3O_4$) was essential for removing any of residual organic material such as solvent or other ligands and converts the surface to active hydroxyl group that are ready to undergo functionalization (silanization). The pretreatment included rinsing the particle in 20 to 40% solution of hydrogen peroxide in sulfuric acid or alternatively in 20 to 40% of $NH_4$ solution in sulfuric acid for at least 5 minutes at ambient conditions or at elevated temperature, preferable at least for 30 minutes at 60° C.

(b) Forming a Tertiary Amine Comprising Two Terpenoid Groups:

Tertiary amine was prepared by reacting primary amine-functionalized particles obtained in step (a) with citral (terpenoid) at 1:10 amine to citral mole ratio and continuous reduction of imine formed in-situ by $NaBH_4$ (reductive amination). The reaction was conducted in dichloromethane at ambient conditions. Subsequently, functionalized particles were recovered by rinsing/drying method in purified water.

(c) Formation of Quaternary Ammonium Compounds Comprising Elongated Alkyl Chain (C8):

In order to obtain the quaternary ammonium derivative, the primary amine-functionalized particles of step (a) were reacted with paraformaldehyde at 1:10 mole ratio of amine to formaldehyde unit and continuous reduction of the imine formed in-situ by $NaBH_4$ (reductive amination). The reaction was conducted in dichloromethane (DCM) for 24 hours and produced a tertiary amine intermediate. The tertiary amine was further alkylated utilizing 1.25 mole eq. of 1-iodooctane in DCM. The reaction was conducted under ambient temperature for 48 hours. Subsequently, quaternary ammonium functionalized particles were recovered by rinsing/drying method.

Example 5: Preparation and Surface Functionalization of Organic Polymeric Core Particles with Cinnamaldehyde Dry polyethylene imine (PEI) was first dissolved in absolute ethanol at 1:10 wt/v ratio. 0.025 mol eq. of 1,5-diiodopentane was added to produce cross-linked PEI particles under 80° C. reflux conditions for 24 hours. The particles were recovered by ethanol evaporation under heating and vacuum conditions, then re-dissolved in DCM. Functionalization was carried out by the addition of 10 mole of cinnamaldehyde to 1 mole eq. of ethylene imine unit and continuous reduction of the imine formed in-situ utilizing $NaBH_4$ (reductive amination). The reaction was conducted in DCM at ambient conditions. Subsequently, the functionalized particles recovered by rinsing/drying method in purified water.

Example 6: Anti-Microbial Activity of Matrix Comprising Functionalized Silica Particles Anti-Microbial Test Conditions—Direct Contact Test Direct contact between bacteria and the tested materials was achieved by applying 10 µl of bacterial suspension on each tested material sample in a set of 8 wells. The plate was incubated at a vertical position for 1 h at 37° C. During this incubation period, the suspension's liquid evaporated and a thin layer of bacteria was obtained, ensuring direct contact between the bacteria and the tested material. The plate was then placed horizontally and 220 µl of brain-heart infusion broth were added to each well containing the material. All tests were done using *Stapilococcus aureus* (*S. aureus*) and *Enterococcus faecalis* (*E. faecalis*) as representative for Graham positive bacteria and *Pseudomonas aeruginosa* (*P. aeruginosa*) as representative for Graham negative bacteria.

The kinetic measurement of bacterial growth was done utilizing temperature controlled microplate spectrophotometer (VERSAmax, Molecular Devices Corporation, Menlo Oaks Corporate Centre, Menlo Park, CA, USA). The microtitre plate was placed in the spectrophotometer, at 37° C. with 5 sec vortex prior to every reading. Bacterial growth was estimated by the OD changes in each well at 650 nm every 20 minutes for 24 hours.

Sample Preparation

1) Polypropylene Comprising Quaternary Ammonium Functionalized Silica Particles

Silica particles of an average diameter of 186 nm functionalized with quaternary dimethyl octyl ammonium were embedded in polypropylene. Samples of polymer films were prepared by hot molding of polypropylene and the functionalized silica particles at 0, 1 and 2% wt/wt of particles. 5×10 mm samples of prepared films were positioned into wells of microtitre plate touching the inside sidewalls of each well.

The anti-bacterial test results demonstrated a consistently low OD (0.1) level during the experiment for the polypropylene samples containing 1 and 2% wt/wt of particles, while the polypropylene sample containing no particles and the control sample containing *S. aureus* demonstrated a significant OD increase (0.7) (FIG. 1).

Figure 2:
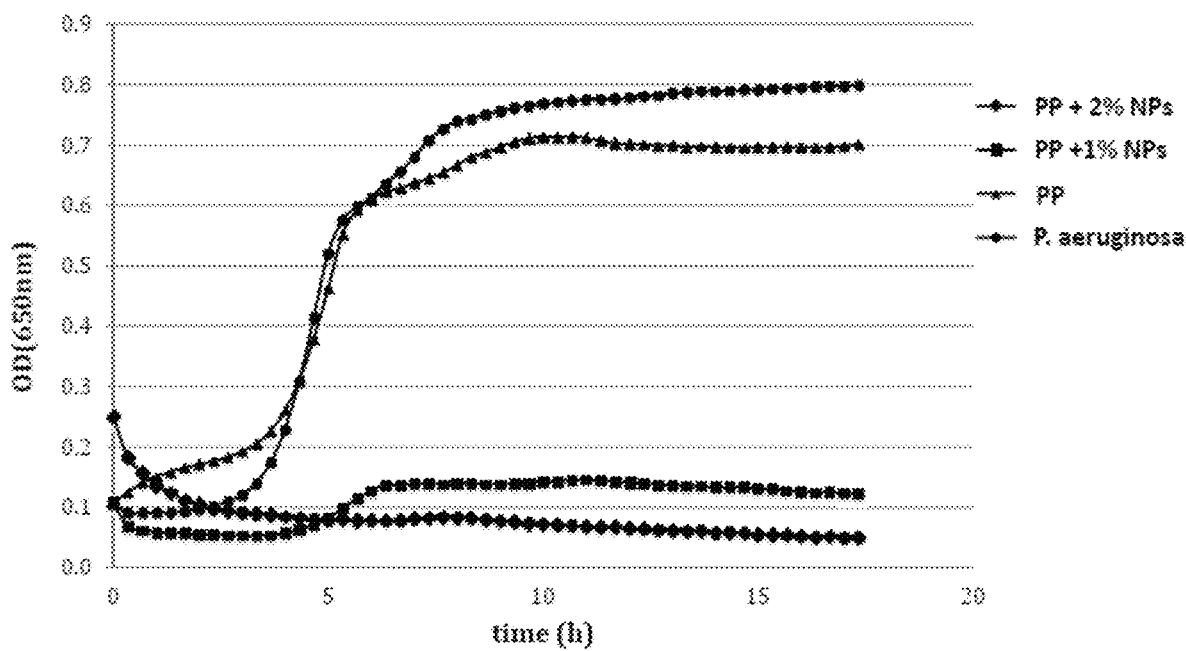
FIG. 2: depicts the anti-microbial activity of a polypropylene matrix without (PP) and with 1% wt/wt (PP+1% NPs) and 2% wt/wt (PP+2% NPs) particles functionalized with dimethyl octyl ammonium groups, against the Graham negative bacteria *Pseudomonas aeruginosa* (*P. aeruginosa*). The embedded particles were 186 nm in average, and the results were compared with the natural growth of *P. aeruginosa*.

Similar results were obtained in the presence of *P. aeruginosa*, where the polypropylene samples containing 2% wt/wt of particles demonstrated a low OD level (0.05) and the sample containing 1% wt/wt of particles showed a slightly higher OD level (0.15). In contrast, the polypropylene sample containing no particles and the control sample containing *P. aeruginosa* demonstrated a significant OD increase (0.7) (FIG. 2).

These results reveal the anti-microbial effect obtained by the modified polypropylene substrate utilizing quaternary ammonium functionalized silica nanoparticles.

2) Poly (Methyl Methacrylate) Comprising Quaternary Amine Functionalized Silica Particles Silica particles of an average diameter of 13 µm functionalized with quaternary dimethyl octyl ammonium were embedded in commercially available dental polymerizable methylmethacrylate (Unifast Trad, GC America inc) at concentration of 0 and 1% wt/wt. The methylmethacrylate was mixed in a silicone crucible at a liquid/powder ratio of 2 g/ml respectively, in accordance to manufacturer's instructions and then allowed to polymerize onto sidewalls of microtiter wells at 37° C. for 24 hours prior to the anti-microbial test.

Figure 3:
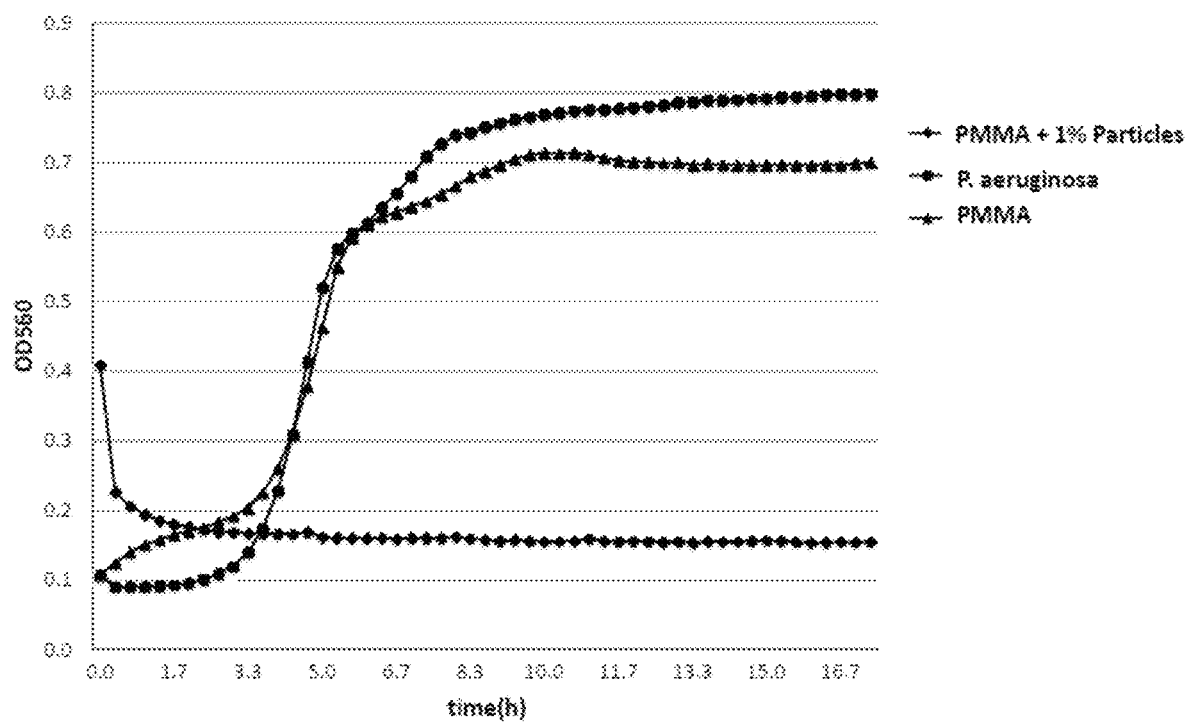
FIG. 3: depicts the anti-microbial activity of a poly (methyl methacrylate) matrix without (PMMA) and with 1% wt/wt silica core particles functionalized with quaternary dimethyl octyl ammonium groups (PMMA+1% NPs), against the Graham negative bacteria *Pseudomonas aeruginosa* (*P. aeruginosa*). The embedded particles were 13 μm in diameter on average, and the results were compared with the natural growth of *P. aeruginosa*.

The anti-bacterial test results demonstrated a consistently low OD (0.1) level during the experiment for the methymethacrylate (PMMA) samples containing 1% wt/wt of particles, while the PMMA sample containing no particles and the control sample containing P. aeruginosa demonstrated a significant OD increase (0.8) (FIG. 3).

Figure 4:
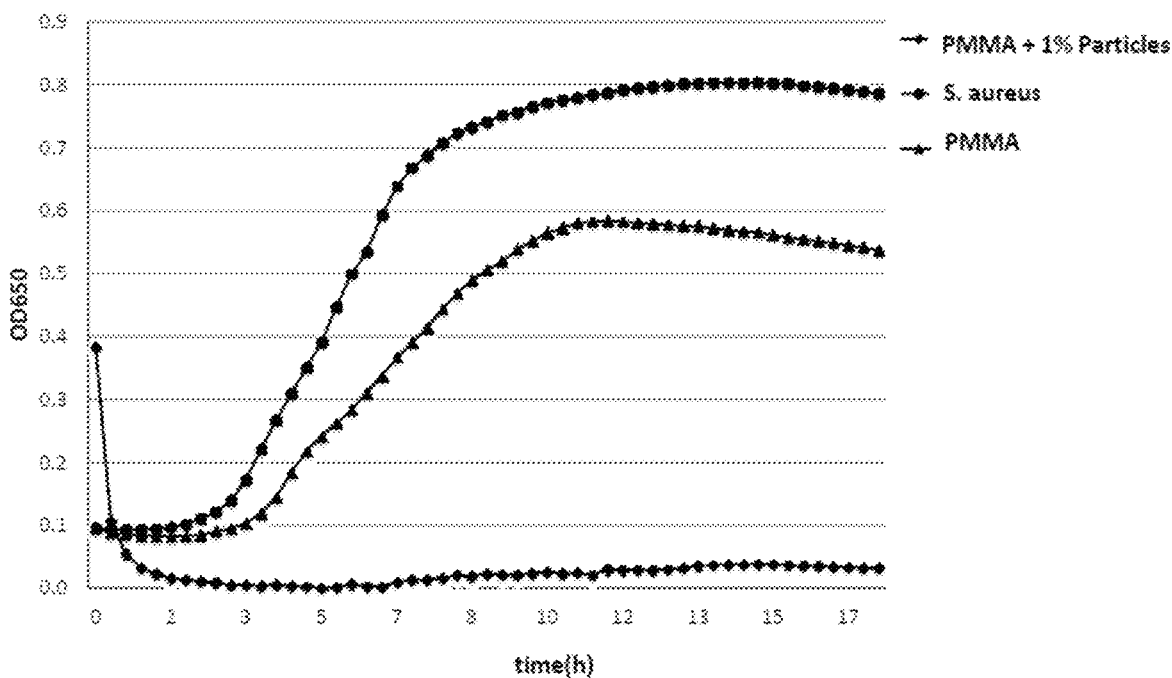
FIG. 4: depicts the anti-microbial activity of a poly (methyl methacrylate) matrix without (PMMA) and with 1% wt/wt silica core particles functionalized with quaternary dimethyl octyl ammonium groups (PMMA+1% NPs), against the Graham positive bacteria *Staphylococcus aureus* (*S. aureus*). The embedded particles were 13 μm in diameter on average, and the results were compared with the natural growth of *S. aureus*.

Similar results were obtained in the presence of S. aureus, where PMMA sample containing 1% wt/wt of particles demonstrated a low OD level (0.1) and the sample containing no particles and the control sample containing S. aureus demonstrated a significant OD increase (0.8) (FIG. 4).

These results reveal the anti-microbial effect obtained by the modified PMMA substrate utilizing quaternary ammonium functionalized silica macro-size particles.

3) Poly (Methyl Methacrylate) Comprising Tertiary Amine Functionalized Silica Particles Silica particles of an average diameter of 186 nm functionalized with di-cinnamyl amine (tertiary amine) were embedded in commercially available dental polymerizable methylmethacrylate (Unifast Trad, GC America Inc.) at concentration of 0 and 1% wt/wt. The methymethacrylate was mixed in a silicone crucible at a liquid/powder ratio of 2 g/ml respectively, in accordance to manufacturer's instructions and then allowed to polymerize onto sidewalls of microtiter wells at 37° C. for 24 hours prior to the anti-microbial test.

Figure 5:
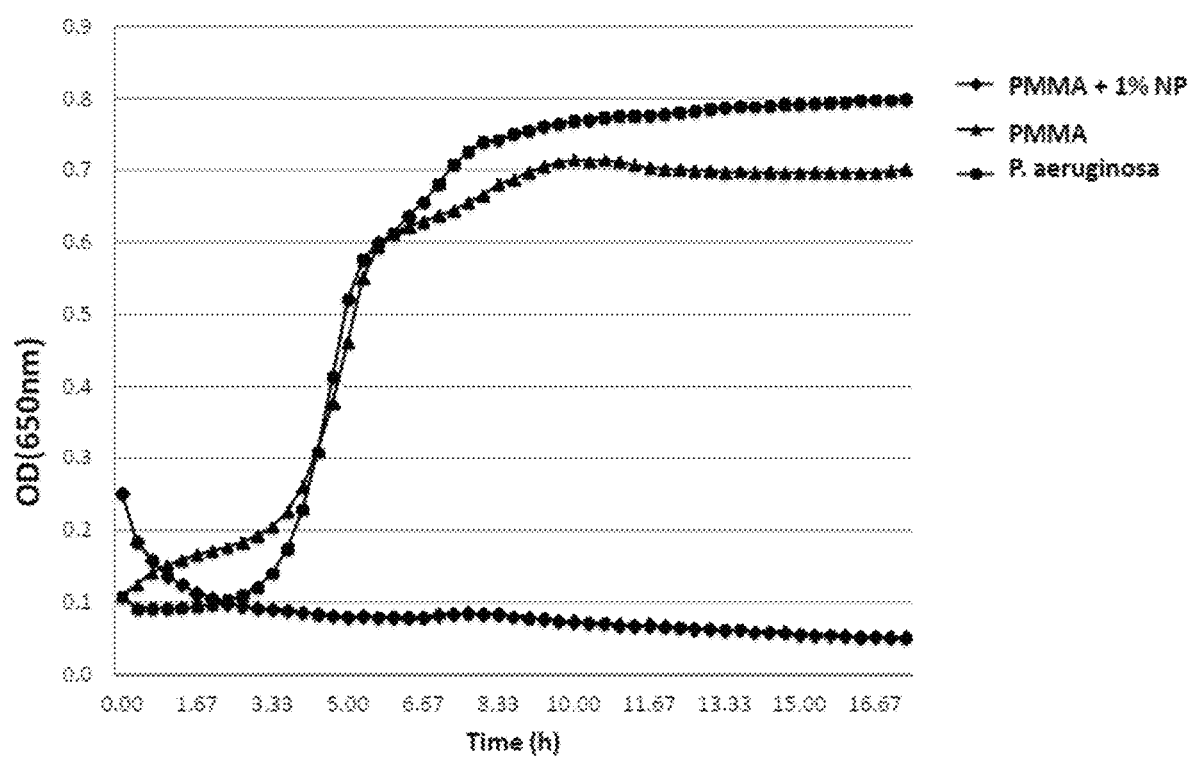
FIG. 5: depicts the anti-microbial activity of a poly (methyl methacrylate) matrix without (PMMA) and with silica core particles functionalized with di-cinnamyl amine groups (PMMA+1% NPs), against the Graham negative bacteria *Pseudomonas aeruginosa* (*P. aeruginosa*). The embedded particles were 186 nm in diameter on average, and the results were compared with the natural growth of *P. aeruginosa*.

The anti-bacterial test results demonstrated a consistently low OD level during the experiment for the methymethacrylate (PMMA) samples containing 1% wt/wt of particles, while the PMMA sample containing no particles and the control sample containing P. aeruginosa demonstrated a significant OD increase (FIG. 5).

Figure 6:
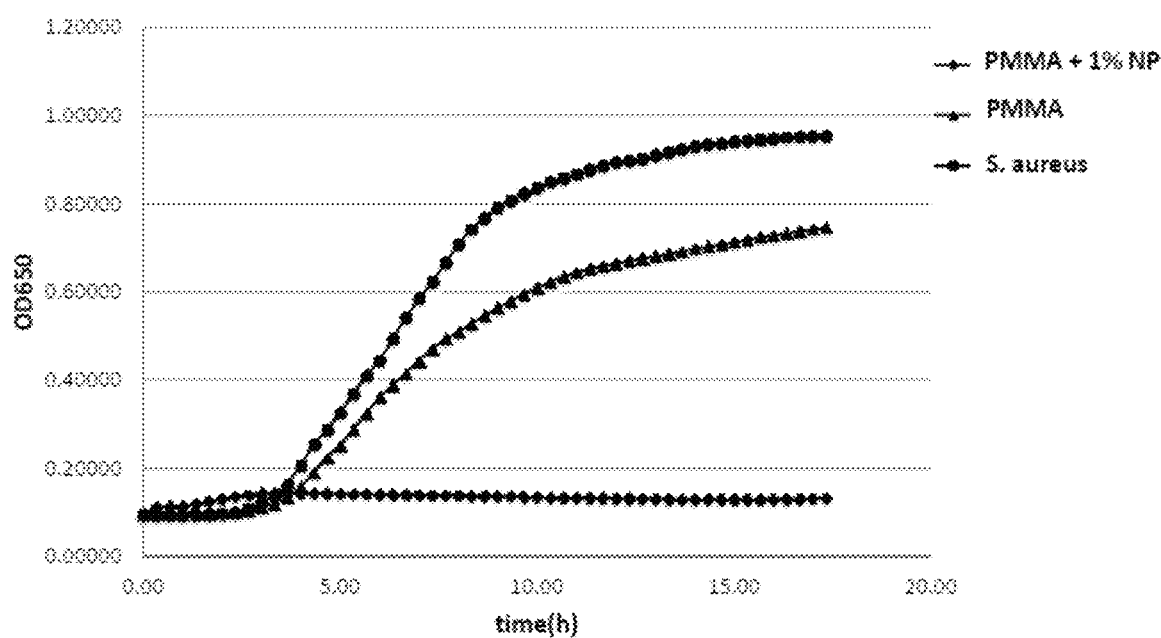
FIG. 6: depicts the anti-microbial activity of a poly (methyl methacrylate) matrix without (PMMA) and with silica core particles functionalized with di-cinnamyl amine groups (PMMA+1% NPs), against the Graham positive bacteria. *Staphylococcus aureus* (*S. aureus*). The embedded particles were 186 nm in diameter on average, and the results were compared with the natural growth of *S. aureus*.

Similar results were obtained in the presence of S. aureus, where PMMA sample containing 1% wt/wt of particles demonstrated a low OD level (0.1) and the sample containing no particles and the control sample containing S. aureus demonstrated a significant OD increase (0.7) (FIG. 6).

These results reveal the anti-microbial effect obtained by the modified PMMA substrate utilizing di-terpenoid (tertiary amine) functionalized silica nanoparticles.

4) Poly (Methyl Methacrylate) Comprising Quaternary Amine Functionalized Magnetite Particles Magnetite ($Fe_3O_4$) particles of an average diameter of 78 nm functionalized with quaternary dimethyl octyl ammonium (prepared as described in Example 3) were embedded in commercially available dental polymerizable methylmethacrylate (Unifast Trad, GC America inc) at concentration of 0, 1 and 2% wt/wt. The PMMA was mixed in a silicone crucible at a liquid/powder ratio of 2 g/ml respectively, in accordance to manufacturer's instructions and then allowed to polymerize onto sidewalls of microtiter wells at 37° C. for 24 hours prior to the anti-microbial test.

Figure 7:
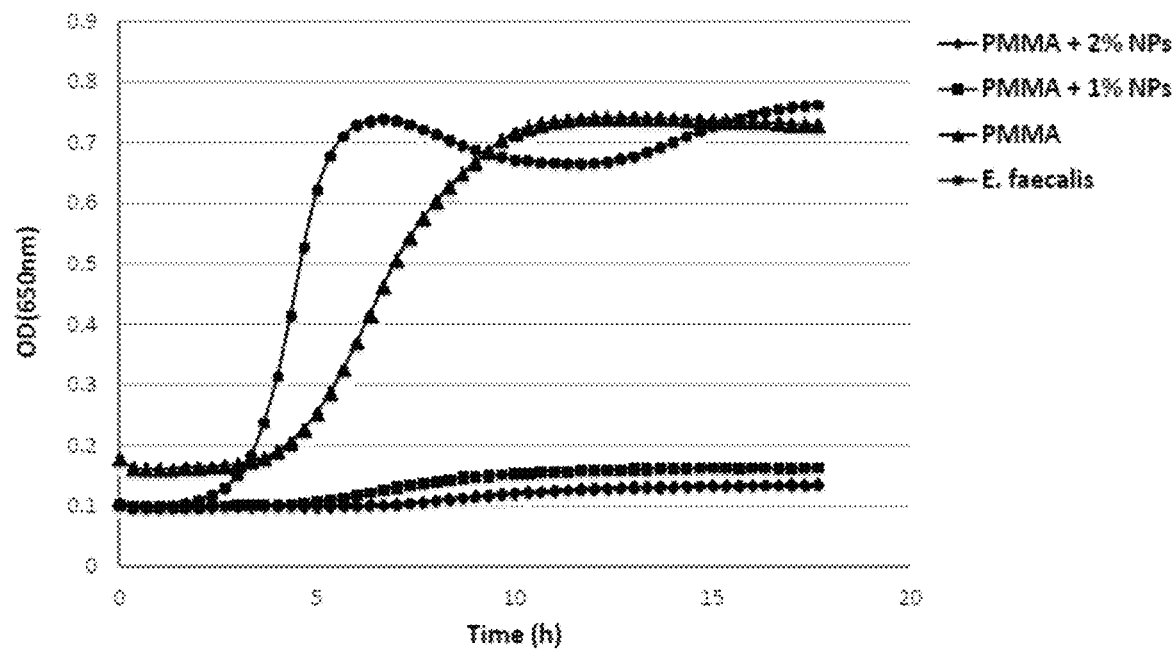
FIG. 7: depicts the anti-microbial activity of a poly (methyl methacrylate) matrix without (PMMA) and with 1% wt/wt (PMMA+1% NPs) or 2% wt/wt (PMMA+2% NPs) Magnetite ($Fe_3O_4$) core particles functionalized with quaternary dimethyl octyl ammonium groups, against the Graham positive bacteria *Enterococcus faecalis* (*E. faecalis*). The embedded particles were 78 nm in diameter on average, and the results were compared with the natural growth of *E. faecalis*.

The anti-bacterial test results demonstrated a consistently low OD level (0.1) during the experiment for the methymethacrylate (PMMA) samples containing 1 and 2% wt/wt of particles, while the PMMA sample containing no particles and the control sample containing E. faecalis demonstrated a significant OD increase (0.8) (FIG. 7).

These results reveal the anti-microbial effect obtained by the modified PMMA substrate utilizing quaternary ammonium functionalized magnetite nanoparticles.

5) Poly (Methyl Methacrylate) Comprising Quaternary Amine Functionalized Silica Particles Silica particles of an average diameter of 186 nm functionalized with quaternary ammonium comprising di-cinnamyl methyl substitutes (prepared as described in Example 4), were embedded in commercially available dental polymerizable methylmethacrylate (Unifast Trad) at concentration of 0, 2 and 3% wt/wt. The PMMA was mixed in a silicone crucible at a liquid/powder ratio of 2 g/ml respectively, in accordance to manufacturer's instructions and then allowed to polymerize onto sidewalls of microtiter wells at 37° C. for 24 hours prior to the anti-microbial test. Both liquid and solid parts of the polymer material were manipulated accordingly to manufacturer's instructions and then allowed to polymerize onto sidewalls of microtiter wells at 37° C. for 24 hours prior to the anti-microbial test.

Figure 8:
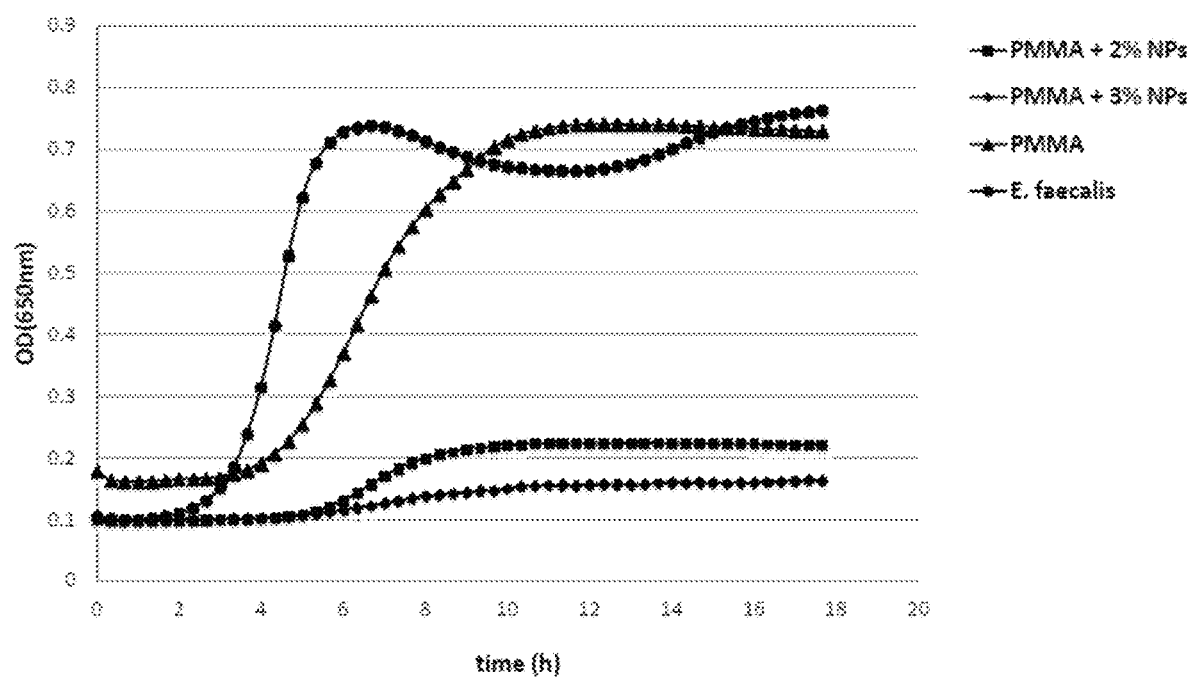
FIG. 8: depicts the anti-microbial activity of a poly (methyl methacrylate) matrix without (PMMA) surface and with 2% wt/wt (PMMA+2% NPs) or 3% wt/wt (PMMA+3% NPs) silica core particles functionalized with di-cinnamyl methyl ammonium groups against the Graham positive bacteria. *Enterococcus faecalis* (*E. faecalis*). The embedded particles were 186 nm in diameter on average, and the results were compared with the natural growth of *E. faecalis*.

The anti-bacterial test results demonstrated a low OD (0.1) level during the experiment for the methymethacrylate (PMMA) samples containing 3% wt/wt of particles, and a slightly higher level for the sample containing 2% wt/wt of particles. In contrast, the PMMA sample containing no particles and the control sample containing E. faecalis demonstrated a significant OD increase (0.7) (FIG. 8).

These results reveal the anti-microbial effect obtained by the modified PMMA substrate utilizing di-terpenoid quaternary ammonium functionalized silica nanoparticles.

Example 7: Mechanical Tests of Resins Comprising Functionalized Particles

Poly methylmethacrylate (Unifast Traci) cylindrical specimens of 0.4 mm in diameter and 10 mm in length were prepared using polypropylene pipe-like molds, Specimens were allowed to polymerize at room temperature for 1 hour within the molds, then stored in DDW at 37° C. for 24 hours prior to testing. Each tested group contained 10 specimens of cured cement with 8% wt/wt NPs. A control group was obtained using the polymer specimens without functionalized particles. Compressive strength test was carried out using universal testing machine (instron 3366, Canton, MA) operated at displacement speed of 1 mm/min. Data was instantly analyzed with Merlin software which calculated the compressive strength and the Young's modulus.

The NPs tested were marked as follows:
1) SiCial—containing 8% wt of silicadioxide particles functionalized with tertiary amine functional group having two cinnamyl substituents with diameter of 186 nm (prepared as defined in Example 4).
2) QPEI—containing 8% wt of dimethyl octyl quaternary ammonium functionalized PEI particles of 24 nm (prepared as defined in Example 5).
3) A sample of unmodified poly methylmethacrylate (PMMA) resin was used as a control.

Figure 9A:
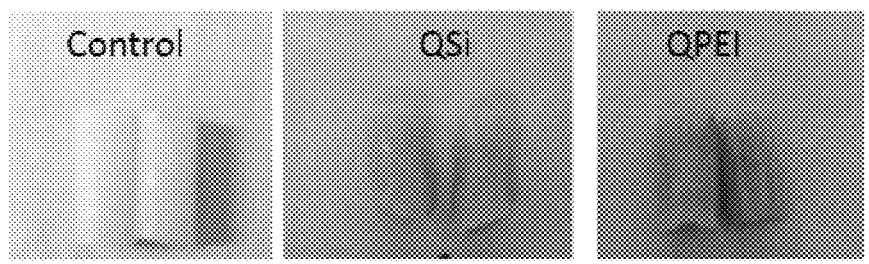
FIGS. 9A-9B: mechanical properties test measuring the young's modulus of modified polymer including functionalized antibacterial particles in comparison to unmodified polymer.
Figure 9B:
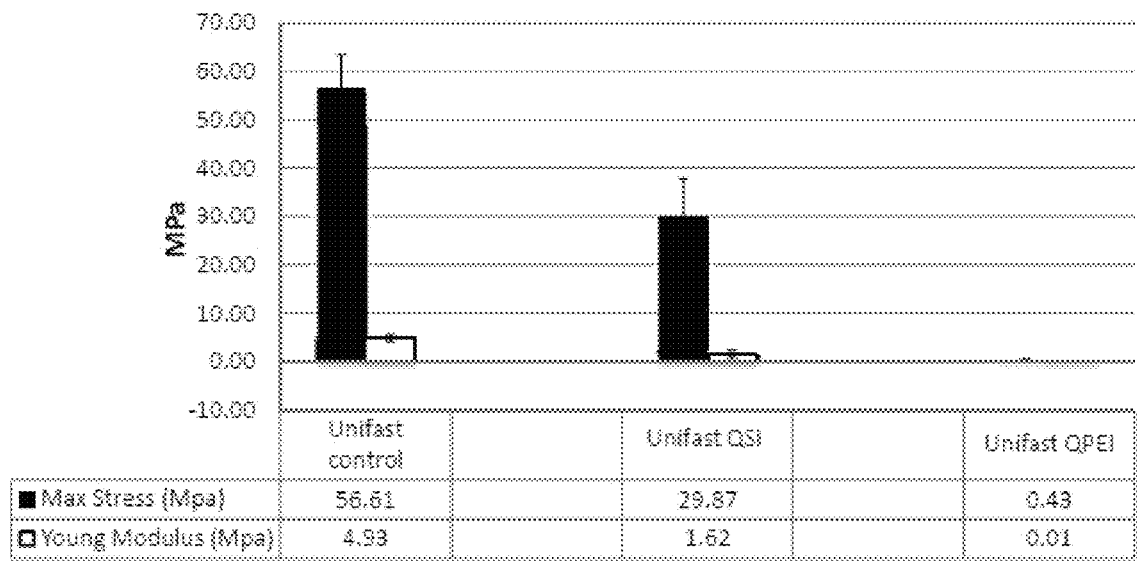

The results demonstrated relatively high stability of the modified acrylate resin comprising the silica based particles under stress conditions. The compressive strength of unmodified PMMA, SiCial and QPEI are 56.61, 78.79 and 0.43 MPa respectively. The embedment of silica functionalized antibacterial particles did not jeopardize the mechanical properties of the resin, and appeared to be advantageous in terms of stress-stability in comparison to the polymeric functionalized resin (QPEI) (FIG. 9B).

Example 8: Antibacterial Test of Resins Comprising Functionalized Particles

The samples described on Example 7 were tested for their antibacterial activity by direct contact test as described herein above (Example 6).

Figure 10A:
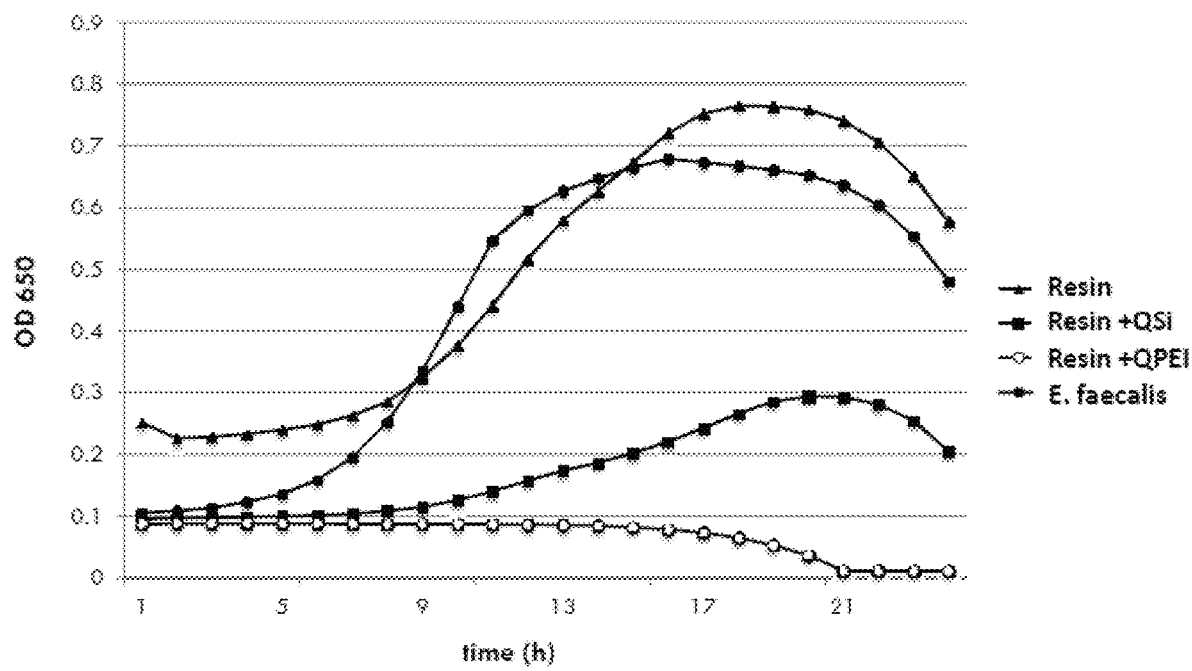
FIGS. 10A-10B: depicts the anti-microbial activity of modified and unmodified specimens of Unifast Trad (a self-cured, methylmothacrylate resin), prepared without (Unifast) or with 8% nanoparticies (NPs) silica+quaternaty dimethyl octyl ammonium group (QSi) and PEI+quaternary dimethyl octyl ammonium (QPEI).
Figure 10B:
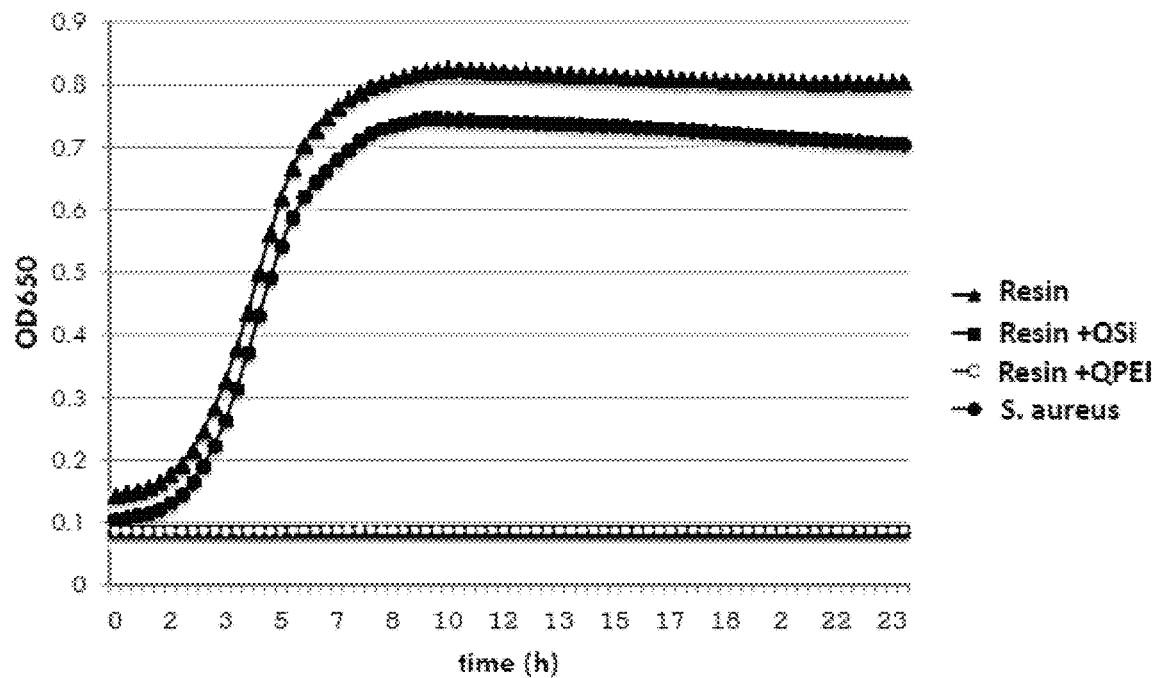

The results demonstrate the potent antibacterial effect of the modified resins due to the embedment of the functionalized silica-based and PEI-based particles compared with the unmodified resin control sample and the natural growth of bacteria as depicted in the presence of *E. faecalis* (FIG. 10A) and *S. aureus* (FIG. 10B).

Example 9: Antibacterial Test by Imprint Method

Three glass slides were coated utilizing spraying of a solution containing functionalized silica based particles onto the hydroxylated glass surface. The silane group anchored the functionalized particles to the slide upon hydrolysis of the leaving groups and the slides were further dried at elevated temperature to allow complete condensation of the particles onto to the surface. The glasses were marked as follows: 1) dimethylamine functionalized silica particles; 2) Tertiary Amine with Two Cinnamyl Groups Functionalized Silica Particles.

*S. aureus* suspension was applied onto each functionalized slide in a homogeneous manner. The slides were placed in contact with blood agar petri dish facing towards the agar for 15 minutes. Subsequently, the slides were removed and the petri dishes were kept in 37° C. for 24 to allow formation of colonies.

Figure 11:
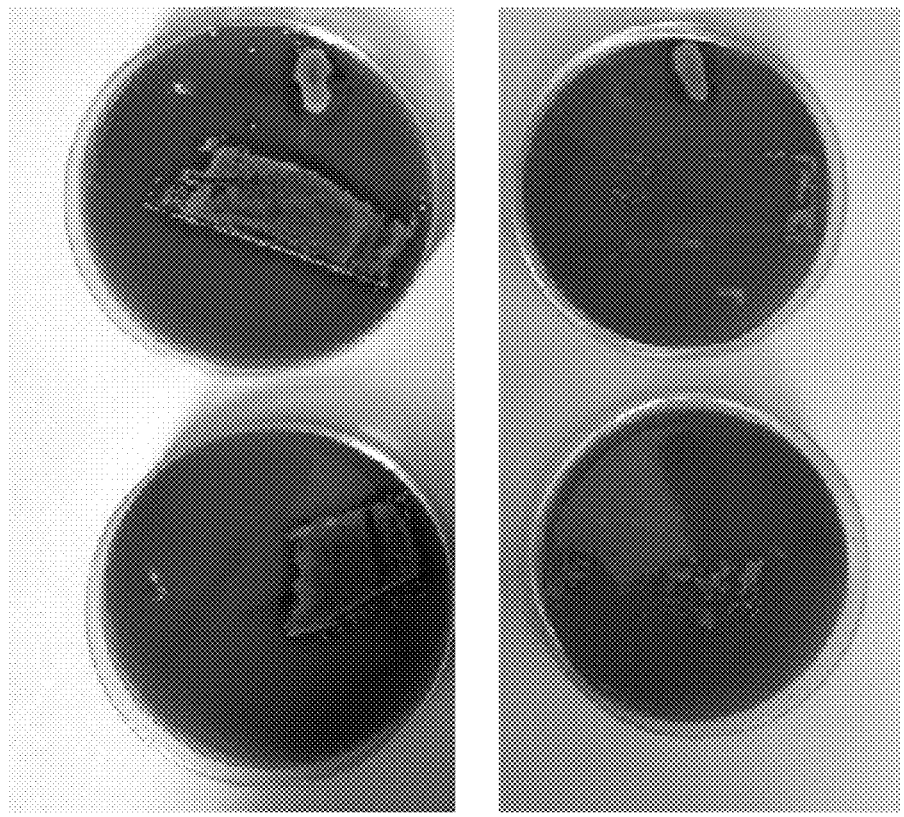
FIG. 11: demonstrates anti-microbial activity as evaluated by an imprint method on blood agar. The samples measured are: 1) dimethylamine functionalized silica particles; and 2) tertiary amine with two cinnamyl groups functionalized silica particles.

The results revealed that no colonies were formed onto the petri dish which came in contact with functionalized slide 2, demonstrating the advantageous antibacterial activity of the tertiary amine comprising two cinnamyl groups (FIG. 11).

Figure 17:
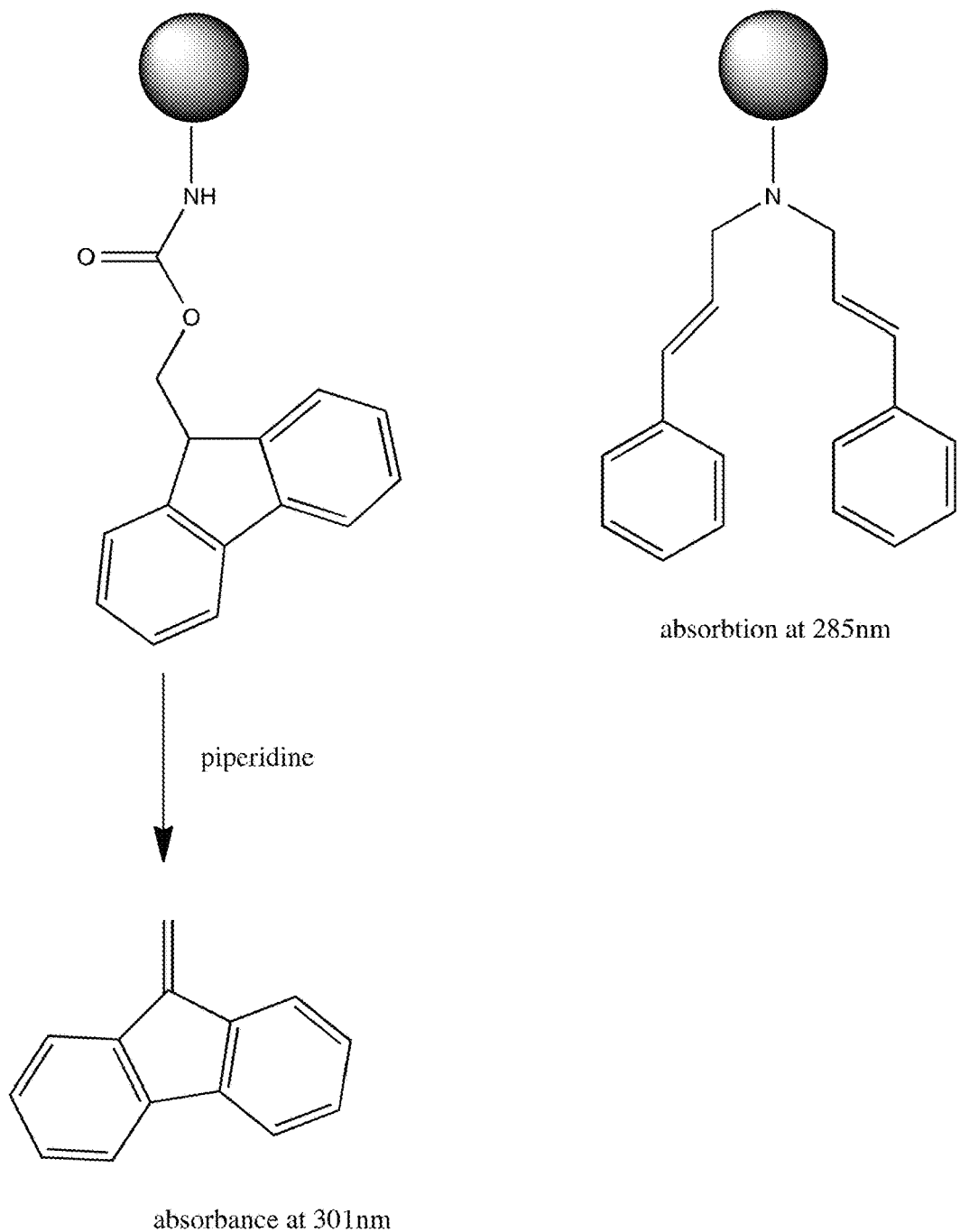
FIG. 17: A scheme, showing methods to determine the load concentration of the anti-microbial group onto the core.

Example 10: Determination of the Loading Degree of Anti-Bacterial Active Groups Onto the Core FIG. 17 presents a scheme of the different methods to determine the load concentration of the anti-microbial group onto the core.

Method 1—degree of amine loading onto particle's surface, 1.0 g of dry amine-functionalized silica particles powder having 180 nm diameter was immersed in 20 ml of dry toluene. Then 0.1 g (1.9 mmol) of Fluorenylmethyloxycarbonyl (Fmoc) chloride were added. The mixture was reacted at 60° C. under continuous stirring for 12 hours. Resulting particles were filtered and rinsed 3 times with 5 ml of N-Methyl-2-pyrrolidone (NMP), then 3 times with 5 ml of diethyl ether and then dried in-vacuo. Detachment of Fmoc was performed by immersing 0.01 g of Fmoc-labeled particles in 2 ml of 20% by volume solution of piperidine in NMP and shaked for 30 min followed by filtration of solvent. This procedure repeated once more and both solutions were combined (to a total of 4 ml solution). Concentration of Fmoc in solution was determined using light absorbance in spectrophotometer at 301 nm and calculated in accordance to Beer's law $A=EbC$, where A is absorbance, E is molar absorption constant ($6300\ cm^{-1}M^{-1}$), b is pathway length (1 cm) and C is molar concentration. Prior to spectrometry readings, solution was diluted at 1:100 ratio in NMP.

Results: $A=1.1$, therefore $C=100\times(1.7\times10^{-4})M=0.017M$. Therefore, N (moles) $=0.017M\times0,004\ L=6.98\times10^{-5}$ moles. Total loading is therefore $6.98\times10^{-5}$ mol/0.01 g$=0.007$ moles/gr. Assuming perfect sphere geometry of particles, the shell surface area of single particles is 102000 $nm^2$ and particle average volume is 3050000 $nm^3$. Particles density calculated using Archimedes method is 2.5 g/($1\times1.0^{21}\ nm^3$), giving a single particle's mass of $7.6\times10^{-16}$ g. Therefore, the loading of functional groups is $((7.6\times10^{-16}\ g)\times(0.007\ moles/g))/102000\ nm^2=5.2\times10^{-23}$ moles/$nm^2$, which is approximately 31 amine/ammonium per $nm^2$.

Method 2—degree of functional tertiary amines substituted with two cinnamyl groups. 0.001 g of 186 nm silica particles functionalized with di-cinnamyl amines were immersed in 100 ml of absolute ethanol. Spectrophotometric reading were taken at the wavelength of 327 nm. E(cinnamaldehyde)$=25118\ cm^{-1}M^{-1}$. All calculations were performed as described in Method 1.

Results: $A=1.5$, therefore total tertiary amines count is $6.0\times10^{-6}$ moles, which is $3.0\times10^{-3}$ moles/g.

Therefore the functional groups loading is approximately 13 amine/ammonium per $nm^2$.

Both methods are applicable for all kinds of inorganic and organic core particles, whereas for organic particles (polymeric particles) the Fmoc functionalization is performed after the cross-linking step.

TABLE 1

Antibacterial activity dependency of polmethylmethacrylate modified particles of the invention. All experiments were performed as in examples 4 and 6.

| Particle | Surface density (units/$nm^2$) | Inhibition of *P. aerginosa* (in $Logs_{10}$) | Inhibition of *S. aureus* (in $Logs_{10}$) |
|---|---|---|---|
| $SiO_2$ core Quaternary ammonium (octyl dimethyl ammonium) func. | 4 | 3 | 4 |
| $SiO_2$ core di-cinnamylamine func. | 4 | 2 | 3 |
| $Fe_3O_4$ core Quaternary ammonium (octyl dimethyl ammonium) func. | 2 | 0 | 3 |
| PEI core Quaternary ammonium (octyl dimethyl ammonium) func. | 4 | 3 | 4 |
| PEI core di-cinnamylamine func. | 4 | 3 | 3 |

As shown in the above table, the poly methylmethacrylate modified particles of the invention showed antibacterial activity for both inorganic and organic cores.

Example 11: Antibacterial Activity of Silica Based Antibacterial Particles of the Current Invention with Tertiary Amine with 2 Cinnamyl Groups or Quaternary Ammonium

TABLE 2 antibacterial activity of polymethylmethacrylate modified with $SiO_2$ particles having tertiary amine with two cinnamyl groups or with $SiO_2$ particles having quaternary ammonium groups.

| | Number of functional groups per square nanometer | S. mutans reduction in Direct Contact Test ($log_{10}$) | E. faecalis reduction in Direct Contact Test ($log_{10}$) |
|---|---|---|---|
| $SiO_2$ with quaternary ammonium | 0.1-0.4 | 3 | 4 |
| $SiO_2$ with tertiary amine with 2 cinnamyl groups | 0.1-0.4 | 2 | 4 |

Table 2 demonstrates the differences between quaternary ammonium functionality and tertiary amines with two cinnamyl groups. It is concluded that quaternary ammonium functionality demonstrate stronger potency to inhibit bacteria growth than tertiary amines with 2 cinnamyl groups.

The foregoing examples of specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The scope and concept of the invention will be more readily understood by references to the claims, which follow.

What is claimed is:

1. A positively charged particle represented by the following structure (3):

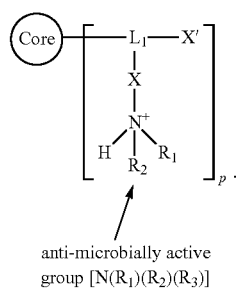

anti-microbially active group [$N(R_1)(R_2)(R_3)$]

wherein
the core is an inorganic material;
$L_1$ is an unsubstituted alkyl siloxane linker or a bond;
$R_1$ is $C_1$-$C_{10}$ alkyl, terpenoid, cycloalkyl, aryl, heterocycle, a conjugated alkyl, alkenyl, alkynyl or any combination thereof;
$R_2$ is $C_1$-$C_{10}$ alkyl, terpenoid, cycloalkyl, aryl, heterocycle, a conjugated alkyl, alkenyl, alkynyl or any combination thereof;
X is a bond, alkyl, alkenyl or alkynyl;
X' is nothing or hydrogen; and
p is the number of chains per one sq nm ($nm^2$) of the core surface, wherein the anti microbial active group is at a surface density of between 0.001-20 anti microbial active groups per one sq nm ($nm^2$) of the core surface of the particle;
wherein if $L_1$ and X are bonds, then the nitrogen is an integral part of the core;
the positively charged particle is balanced by a counter anion; and
at least one of $R_1$, or $R_2$, is $C_4$-$C_8$ alkyl, or alkenyl or alkynyl having at least four carbons, or terpenoid, cycloalkyl, aryl or heterocycle having at least six carbons.

2. The particle of claim 1, wherein the anti microbial active group is at a surface density of between 1-20 anti microbial active groups per one sq nm ($nm^2$) of the core surface of the particle.

3. The particle of claim 1 wherein either $R_1$ is a terpenoid, $R_2$ is a terpenoid, or both $R_1$ and $R_2$ are a terpenoid.

4. The particle of claim 1, wherein the particle is made by chemically binding a chemical represented by the structure of formula (IA)

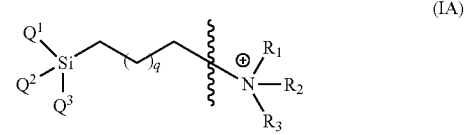

to the core surface of the inorganic core through the silicon side of the chemical structure represented by formula (IA)
wherein
$Q^1$, $Q^2$ and $Q^3$ are independently selected from the group consisting of alkoxy, methyl, ethyl, hydrogen, sulfonate and halide, wherein at least one of $Q^1$, $Q^2$ and $Q^3$ is selected from ethoxy, methoxy, sulfonate and halide;
q is an integer between 1 and 16;
$R_1$ and $R_2$ are independently linear or branched $C_1$-$C_{24}$ alkyl, terpenoid, cycloalkyl, aryl, heterocycle, conjugated $C_1$-$C_{24}$ alkenyl, $C_1$-$C_{24}$ alkenyl, $C_1$-$C_{24}$ alkynyl or any combination thereof; and
wherein at least one of $R_1$, or $R_2$, is $C_4$-$C_8$ alkyl, or alkenyl or alkynyl having at least four carbons, or terpenoid, cycloalkyl, aryl or heterocycle having at least six carbons, and
$R_3$ is hydrogen.

5. The particle according to claim 1, wherein the inorganic material is selected from silica, glasses or ceramics of silicate ($SiO_4^{-4}$) a metal or a metal oxide.

6. The particle according to claim 5, wherein the inorganic material is silica, and the silica is selected from amorphous silica, dense silica, aerogel silica, porous silica or mesoporous silica.

7. The particle according to claim 1, wherein said core has a solid uniform morphology with low porosity or a porous morphology having pore size diameter of between about 1 to about 100 nm.

8. The particle according to claim 1, wherein the particle has a diameter between about 5 to about 100,000 nm.

9. The particle of claim 3, wherein the terpenoid is a cinnamyl group derived from cinnamaldehyde, cinnamic acid or cinnamyl alcohol; a bornyl group derived from camphor, bornyl halide or bornyl alcohol; a terpenoid group derived from citral; a terpenoid group derived from curcumin, a terpenoid group derived from citronellal or a terpenoid group derived from perillaldehyde; or wherein the terpenoid is selected from the group consisting of:

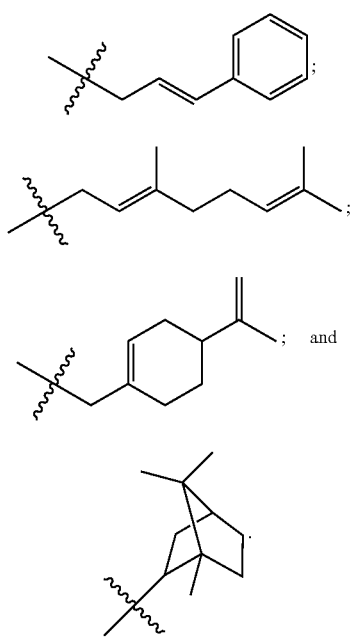

10. A composition comprising a liquid or solid matrix embedding a plurality of particles according to claim 1, wherein the particles are embedded in the matrix through covalent or non-covalent interactions, and, optionally, wherein said matrix is a polymeric matrix comprising a thermoplastic polymer.

11. A packaging composition comprising the composition of claim 10, wherein the packaging composition is for the packaging of food, beverage, pharmaceutical ingredients, laboratory devices, medical devices, surgical equipment before operation, pre operation equipment, cosmetics, and sterilized equipment/materials used in industry and medicine.

12. The composition of claim 10, wherein the composition is a pharmaceutical composition in the form of a cream, an ointment, a paste, a dressing or a gel.

13. The composition of claim 10, wherein the particles are homogeneously distributed on the outer surface of the matrix at a surface concentration of between about 0.1 to about 100 particles per sq. μm.

14. A tooth paste, a tooth pick, dental floss, a post hygienic treatment dressing or gel, a mucosal adhesive paste, a toothbrush, a dental adhesive, a dental restorative composite material for filling tooth decay cavities, a dental restorative endodontic filling material for filling root canal space in root canal treatment, a dental restorative material used for provisional and final tooth restorations or tooth replacement, a dental inlay, a dental onlay, a crown, a partial denture, a complete denture, a dental implant or a dental implant abutment comprising the particle according to claim 1.

15. The particle according to claim 1, for use in inhibiting or preventing biofilm formation or for use in inhibiting bacteria within the oral cavity.

16. A pharmaceutical composition according to claim 12, for use in inhibiting bacteria or inhibiting or preventing biofilm formation.

17. The particle of claim 1, wherein said particle is intended for administration into an oral cavity, and wherein either (a) said particle is in a composition or article selected from the group consisting of a tooth paste, a mouthwash, a tooth pick, dental floss, a post hygienic treatment dressing or gel, a mucosal adhesive paste, and a toothbrush, and/or (b) said particle is intended to be applied to oral hard tissues, oral soft tissues and artificial surfaces in the oral cavity.

18. The particle of claim 1, wherein said particle is intended for administration into an oral cavity or is intended to be used in combination with a medical device selected from the group consisting of: a dental adhesive, a dental restorative composite material for filling tooth decay cavities, a dental restorative endodontic filling material for filling root canal space in root canal treatment, a dental restorative material used for provisional and final tooth restorations or tooth replacement, a dental inlay, a dental onlay, a crown, a partial denture, a complete denture, a dental implant a dental implant abutment, and a cement, wherein said cement is used to permanently cement crowns, bridges, onlays, partial dentures and orthodontic appliances onto tooth enamel and dentin.

\* \* \* \* \*